United States Patent
Kogure et al.

(10) Patent No.: US 9,526,791 B2
(45) Date of Patent: Dec. 27, 2016

(54) WEAKLY ACIDIC PH-RESPONSIVE PEPTIDE AND LIPOSOME CONTAINING SAME

(71) Applicant: Taiho Pharmaceutical Co., Ltd., Tokyo (JP)

(72) Inventors: Kentaro Kogure, Otsu (JP); Susumu Hama, Otsu (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/430,723

(22) PCT Filed: Oct. 21, 2013

(86) PCT No.: PCT/JP2013/078497
§ 371 (c)(1),
(2) Date: Mar. 24, 2015

(87) PCT Pub. No.: WO2014/065245
PCT Pub. Date: May 1, 2014

(65) Prior Publication Data
US 2015/0250893 A1    Sep. 10, 2015

(30) Foreign Application Priority Data

Oct. 22, 2012  (JP) ................. 2012-233011

(51) Int. Cl.
| | | |
|---|---|---|
| A61K 38/00 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 14/00 | (2006.01) | |
| C07K 16/00 | (2006.01) | |
| C07K 17/00 | (2006.01) | |
| A61K 47/42 | (2006.01) | |
| A61K 9/00 | (2006.01) | |
| A61K 9/127 | (2006.01) | |

(52) U.S. Cl.
CPC ............ *A61K 47/42* (2013.01); *A61K 9/0019* (2013.01); *A61K 9/127* (2013.01); *C07K 14/00* (2013.01); *C07K 14/001* (2013.01)

(58) Field of Classification Search
CPC .......... A61K 38/00; C07K 16/00; C07K 14/00
See application file for complete search history.

(56) References Cited

U.S. PATENT DOCUMENTS

2003/0224037 A1    12/2003    Eriguchi et al.

FOREIGN PATENT DOCUMENTS

| JP | 2004010481 A | 1/2004 |
|---|---|---|
| JP | 2004523531 A | 8/2004 |
| JP | 2008214324 A | 9/2008 |
| WO | 02/059147 A2 | 8/2002 |
| WO | 2012/147714 A1 | 11/2012 |

OTHER PUBLICATIONS

Hideyoshi et al., English translation (machine translated), JP2008214324, published on Sep. 18, 2008.*
Guo et al., "Core/Shell pH-Sensitive Micelles Self-Assembled from Cholesterol Conjugated Oligopeptides for Anticancer Drug Delivery", AIChE Journal, 2010, vol. 56(7), pp. 1922-1931.
Kyte et al., "A Simple Method for Displaying the Hydropathic Character of a Protein", J. Mol. Biol., 1982, vol. 157, pp. 105-132.
Oh et al., "pH-sensitive properties of surface charge-switched multifunctional polymeric micelle", International Journal of Pharmaceutics, 2009, vol. 376, pp. 134-140.
Turk et al., "Characterization of a novel pH-sensitive peptide that enhances drug release from folate-targeted liposomes at endosomal pHs", Biochimica et Biophysica Acta, 2002, 1559, pp. 56-68.
Wu et al, "Targeting of early inflammatory metastatic sites by using drug-loaded polymeric micelles", Annual Conference of the Japan Drug Delivery System Research Society Gakujutsu Shukai Program Yokoshu, 28th, Jun. 5, 2012, p. 135.
Yu et al., "Enhanced transfection efficiency of a systemically delivered tumor-targeting immunolipoplex by inclusion of a pH-sensitive histidylated oligolysine peptide", Nucleic Acids Research, 2004, vol. 32(5), e48, pp. 1-10.
International Search Report cited in PCT/JP2013/078497 dated Dec. 24, 2013, 3 pages.
Japanese Office Action cited in 2014-543288 mailed on Jan. 5, 2016, 6 pages.
W Zhang et al., "Design of acid-activated cell-penetrating peptide for delivery of active molecules into cancer cells", Bioconjugate Chemistry, vol. 22, 2011. pp. 1410-1415 (2011).
Extended European Search Report dated Mar. 2, 2016 for the corresponding EP Patent Application No. 13848530.5, 6 pages.

* cited by examiner

*Primary Examiner* — Hasan Ahmed
*Assistant Examiner* — Kaipeen Yang
(74) *Attorney, Agent, or Firm* — Rothwell, Figg, Ernst & Manbeck, P.C.

(57) ABSTRACT

A problem to be solved by the present invention is to provide a peptide compound for producing a drug delivery carrier capable of releasing a target substance in a weakly acidic pH environment. The present invention provides a peptide compound comprising a hydrophilic amino acid block and a hydrophobic amino acid block; [1] the peptide compound containing 24 to 36 amino acids in total; [2] the hydrophilic amino acid block containing 4 to 10 amino acids in total and having an average hydropathy index of −3.0 to −1.0; and [3] the hydrophobic amino acid block containing 20 to 32 amino acids in total, containing one or more His residues, and having an average hydropathy index of 1.0 to 2.5.

16 Claims, 14 Drawing Sheets

WEAKLY ACIDIC PH-RESPONSIVE PEPTIDE AND LIPOSOME CONTAINING SAME

CROSS REFERENCE TO RELATED APPLICATION

This application is a 35 U.S.C. 371 National Phase Entry Application from PCT/JP2013/078497, filed Oct. 21, 2013, which claims the benefit of Japanese Patent Application No. 2012-233011 filed on Oct. 22, 2012, the disclosure of which is incorporated herein in its entirety by reference.

CROSS-REFERENCE TO RELATED APPLICATION

This application claims priority to Japanese Patent Application No. 2012-233011 filed on Oct. 22, 2012, the disclosure of which is incorporated herein by reference in its entirety.

TECHNICAL FIELD

The present invention relates to a weakly acidic pH-responsive peptide and a liposome containing the peptide.

BACKGROUND ART

In cancer chemotherapy, attempts have been made to develop a DDS to improve specificity; however, almost none of these attempts focus on the tumor environment. Specifically, tumor tissues are in a special environment having a pH (a pH around 6.5) lower than that of physiological conditions (a pH around 7.4). However, drug delivery carriers that act in a tumor tissue-specific manner in such a way as to respond to this small pH change have yet to be developed. Until now, in anticipation of the EPR effect (Enhanced Permeation and Retention effect), polyethylene glycol (PEG), which is a hydrophilic macromolecule, has been used to modify the surface of liposomes, etc., and the modified liposomes have been used as a carrier of, for example, anticancer drugs (e.g., Patent Literature (PTL) 1). However, drug release from such a PEG-modified carrier after delivery to tumor tissues is rate-limiting, and the drug cannot be effectively released in the tumor tissues. The peptide-liposome complex disclosed in PTL 2 retains a positive charge due to the presence of basic amino acid (lysine or arginine) at the N-terminal region, and a change in charge does not occur depending on pH; sufficient blood-circulating properties can thus not be expected.

Non-Patent Literature (NPL) 1 uses His segments as a pH-responsive region. According to the technique disclosed in NPL 1, a drastic decrease in the pH of the external environment from 7.4 to 5.0 causes a neutral His to be positively charged, and the thus-increased electrostatic repulsion causes disruption of micelles. However, a His would not sufficiently be protonated alone at a weakly acidic pH of 6.5; therefore, causing charge reversal is difficult. For this reason, drug release associated with the disruption of micelles at a pH of 6.5 cannot be expected.

NPL 2 discloses pH-responsive micelles whose surface charge changes from negative to positive when dimethylmaleic acid chemically bonded to a lysine segment at a terminal of a block polymer is dissociated due to a decrease in pH. In the peptide disclosed in NPL 2, dissociation of the dimethylmaleic acid causes exposure of positively charged lysine residues; even if the pH is increased, such a state does not return to the original state.

CITATION LIST

Patent Literature

PTL 1: JP2004-10481A
PTL 2: JP2004-523531A

Non-Patent Literature

NPL 1: AIChE Journal, Vol. 56, No. 7, 2010, pp. 1922-1931
NPL 2: International Journal of Pharmaceutics, 376, 2009, pp. 134-140

SUMMARY OF INVENTION

Technical Problem

An object of the present invention is to provide a peptide compound for producing a drug delivery carrier capable of releasing a target substance in a weakly acidic pH environment such as cancer tissues.

Solution to Problem

The present invention provides the following items (1) to (10), which are directed to a peptide compound, a liposome comprising the peptide compound, or a substance induction agent using the liposome.
(1) A peptide compound comprising a hydrophilic amino acid block and a hydrophobic amino acid block;
  [1] the peptide compound containing 24 to 36 amino acids in total;
  [2] the hydrophilic amino acid block containing 4 to 10 amino acids in total and having an average hydropathy index of −3.0 to −1.0; and
  [3] the hydrophobic amino acid block containing 20 to 32 amino acids in total, containing one or more His residues, and having an average hydropathy index of 1.0 to 2.5.
(2) The peptide compound according to (1), wherein the hydrophilic amino acid block has an average hydropathy index of −2.0 to −1.5; and
  the hydrophobic amino acid block has an average hydropathy index of 1.5 to 2.0.
(3) The peptide compound according to (1) or (2), wherein the hydrophilic amino acid block comprises an amino acid having a hydropathy index of −3.0 or less and an amino acid having a hydropathy index of 0 to −1.0; and
  the hydrophobic amino acid block comprises His and an amino acid having a hydropathy index of higher than 0.
(4) The peptide compound according to any one of (1) to (3), wherein the amino acids constituting the hydrophilic amino acid block are His or Glu, and Gly; and
  the amino acids constituting the hydrophobic amino acid block are His and at least one amino acid selected from the group consisting of Leu, Ala, Met, Cys, Phe, Val, and Ile.
(5) The peptide compound according to any one of (1) to (4), wherein the hydrophilic amino acid block has a peptide sequence containing 0 to 5 His residues; and
  the hydrophobic amino acid block has a peptide sequence containing 1 to 8 His residues.
(6) The peptide compound according to any one of (1) to (5), wherein the hydrophilic amino acid block is represented by the following formula (I):

$$(AA_1)(AA_2)(AA_3)(AA_4) \qquad (I)$$

wherein any two of $AA_1$, $AA_2$, $AA_3$, and $AA_4$ are His or Glu, and the other two are Gly; and the hydrophobic amino acid block contains 5 to 8 units represented by the following formula (II):

  (II)

wherein $AA_5$, $AA_6$, $AA_7$, and $AA_8$ are the same or different, and each represents His, Leu, or Ala, with the proviso that at least one of the units of the formula (II) contains one or two His residues; each unit may have the same or different amino acid sequence.

(7) A liposome comprising the peptide compound according to any one of (1) to (6), and a lipid.

(8) The liposome according to (7), wherein the liposome comprises 1 to 10 mol % of the peptide compound according to any one of (1) to (6) based on the total amount of lipids in the liposome.

(9) The liposome according to (8), wherein the liposome is a cationic liposome.

(10) The liposome according to any one of (7) to (9), wherein the liposome encapsulates a target substance.

(11) A pharmaceutical composition comprising the liposome according to any one of (7) to (10).

(12) An antitumor agent comprising the liposome according to any one of (7) to (10).

(13) A method for preventing or treating cancer, comprising the step of administering, to a mammal, the liposome according to any one of (7) to (10) in an amount effective to prevent or treat cancer.

(14) Use of the liposome according to any one of (7) to (10) for production of a cancer preventive or therapeutic agent.

(15) The liposome according to any one of (7) to (10), which is used to prevent or treat cancer.

Advantageous Effects of Invention

The present invention can provide a liposome capable of releasing an encapsulated low-molecular target substance in a weakly acidic cellar environment (a pH of about 6.5), while not releasing the target substance under physiological conditions (a pH of about 7.4).

The liposome of the present invention can release a target substance in the above-mentioned weakly acidic region to make the substance act therein, and can thus provide an excellent drug delivery system.

The liposome of the present invention can retain the encapsulated target substance under physiological conditions, i.e., pH 7.4, and can sensitively respond even to a weakly acidic pH of 6.5. For this reason, after reaching a tumor as a result of the EPR effect, the electrostatic repulsion of the hydrophilic block and/or a decrease in the hydrophobic interaction of the hydrophobic block are induced under weakly acidic conditions in the tumor-surrounding environment; the liposome of the present invention thereby releases the encapsulated target substance. As such, the liposome of the present invention is highly useful.

DESCRIPTION OF EMBODIMENTS

Figure 1A:
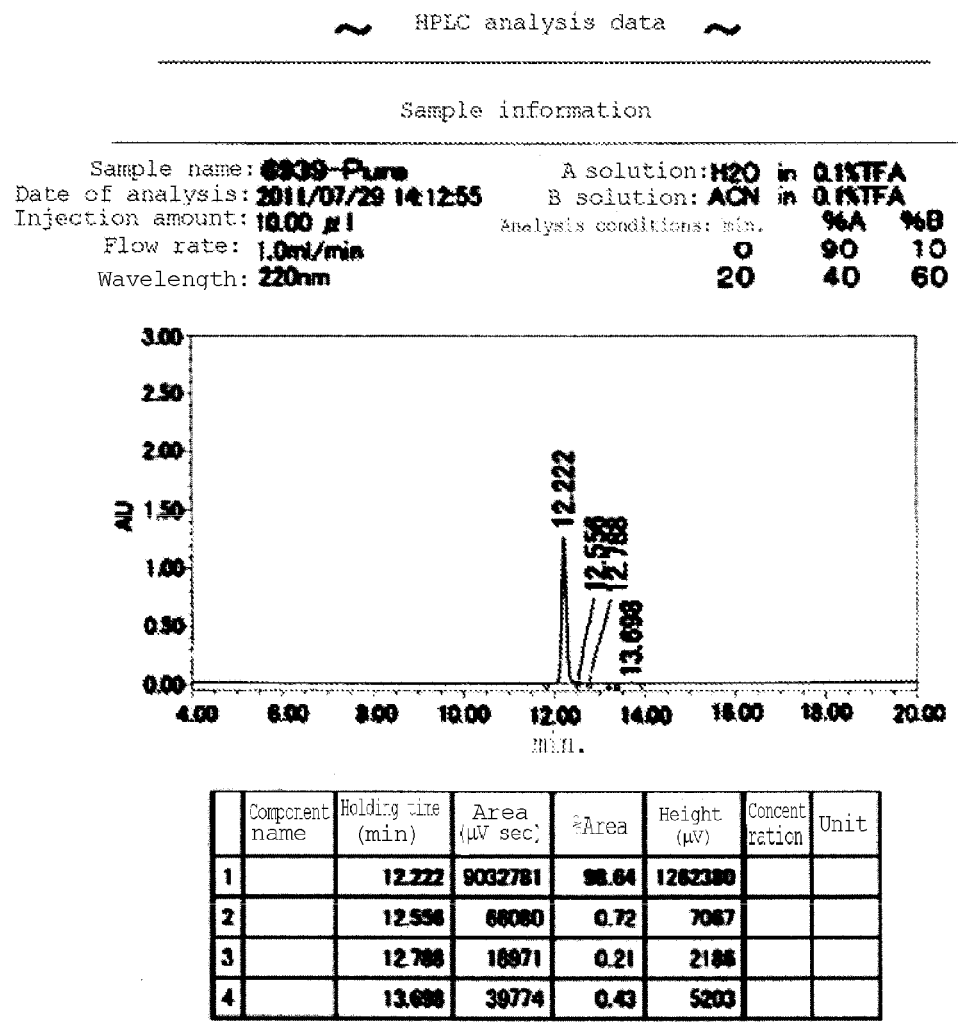
FIG. 1A shows the HPLC results of peptide compound 1 (SEQ ID NO: 1) obtained in Example 1.

The liposome of the present invention comprises a peptide compound and a liposome-forming component.

The peptide compound of the present invention comprises a hydrophilic amino acid block and a hydrophobic amino acid block, and contains 24 to 36, preferably 24 to 32, and more preferably 24 to 28 amino acids in total. The hydrophilic amino acid block contains 4 to 10, and preferably 4 to 8 amino acids in total. The hydrophobic amino acid block contains 20 to 32, and preferably 20 to 24 amino acids in total.

The peptide compound of the present invention comprises one hydrophilic amino acid block and one hydrophobic amino acid block that are bonded by a peptide bond. Either of the amino acid blocks may be located on the N-terminal side; however, it is preferable that the hydrophilic amino acid block is located on the N-terminal side.

Moreover, the hydrophobic amino acid block of the peptide compound of the present invention has one or more His residues; however, in terms of the responsiveness to weak acidity, it is essential that amino acids, including His, having a hydropathy index of −3.0 or less are not adjacent to each other. Furthermore, the sequence of the peptide compound preferably has 1 to 13 His residues.

The hydrophilic amino acid block and the hydrophobic amino acid block, which constitute the peptide compound of the present invention, have specific average hydropathy indices. The hydropathy index of amino acids used in the present invention is described, for example, in J. Mol. Biol., (1982) 157, pp. 105-132, and indicates the degree of hydrophobicity specific to each of the amino acids constituting the organisms (see Table 1). The average hydropathy index is described, for example, in Molecular Medicine, 4: 240-257, 1998, and is obtained by dividing the sum of the hydropathy indices of amino acids in each of the following blocks by the number of amino acids.

TABLE 1

| Amino acid (abbr.) | Hydropathy index | Amino acid | Hydropathy index |
|---|---|---|---|
| Isoleucine (Ile, I) | 4.5 | Serine (Ser, S) | −0.8 |
| Valine (Val, V) | 4.2 | Tyrosine (Tyr, Y) | −1.3 |
| Leucine (Leu, L) | 3.8 | Proline (Pro, P) | −1.6 |
| Phenylalanine (Phe, F) | 2.8 | Histidine (His, H) | −3.2 |
| Cysteine (Cys, C) | 2.5 | Glutamic add (Glu, E) | −3.5 |
| Methionine (Met, M) | 1.9 | Glutamine (Gln, Q) | −3.5 |
| Alanine (Ala, A) | 1.8 | Asparaginic acid (Asp, D) | −3.5 |
| Glycine (Gly, G) | −0.4 | Asparagine (Asn, N) | −3.5 |
| Threonine (Thr, T) | −0.7 | Lysine (Lys, K) | −3.9 |
| Tryptophan (Trp, W) | −0.9 | Arginine (Ang, R) | −4.5 |

In a preferred embodiment of the present invention, the hydrophilic amino acid block comprises amino acids having a hydropathy index of 0 or less, and the hydrophobic amino acid block comprises His and an amino acid having a hydropathy index of higher than 0. Therefore, the border between the hydrophilic amino acid block and the hydrophobic amino acid block is determined by the hydropathy index of amino acids other than His. His located on the border is contained in the hydrophilic amino acid block.

The hydrophilic amino acid block that constitutes the peptide compound of the present invention may have any combination of amino acids having an average hydropathy index of −3.0 to −1.0, and preferably −2.0 to −1.5. Preferred is a combination of an amino acid having a hydropathy index of −3.0 or less and an amino acid having a hydropathy index of 0 to −1.0; more preferred is a combination of His or Glu, and Gly; and even more preferred is a combination of His and Gly. Further, the peptide sequence of the hydrophilic amino acid block preferably has 0 to 5 His residues. More specifically, particularly preferred is a hydrophilic amino acid block represented by the following formula (I):

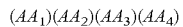  (I)

wherein any two of $AA_1$, $AA_2$, $AA_3$, and $AA_4$ are His or Glu, and the other two are Gly (particularly preferably, any two are His, and the other two are Gly).

The hydrophobic amino acid block that constitutes the peptide compound of the present invention may have any combination of amino acids having an average hydropathy index of 1.0 to 2.5, and preferably 1.5 to 2.0. Preferred is a combination of His and an amino acid having a hydropathy index of higher than 0; more preferred is a combination of His and any amino acid selected from Leu, Ala, Met, Cys, Phe, Val, and Ile; and particularly preferred is a combination of His and either of Leu and Ala, which are amino acids that are likely to have an α-helix structure. Further, the peptide sequence of the hydrophobic amino acid block preferably has 1 to 8 His residues. More specifically, particularly preferred is a hydrophobic amino acid block containing 5 to 8 units represented by the following formula (II):

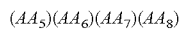  (II)

wherein $AA_5$, $AA_6$, $AA_7$, and $AA_8$ are the same or different, and each represents His, Leu, or Ala, with proviso that two His residues between the units or in each unit are not adjacent to each other; each unit may have the same or different amino acid sequence.

Particularly preferred examples of the peptide compound of the present invention include the following:

His-Gly-His-Gly-Leu-Ala-Leu-Leu-Ala-His-Ala-Leu-Leu-Ala-His-Ala-Ala-Leu-Ala-His-Ala-Ala-Leu-Ala (SEQ ID NO: 1);

Gly-His-His-Gly-Leu-Ala-Leu-Leu-His-Ala-Leu-His-Leu-Ala-Ala-Ala-Ala-Leu-His-Ala-Ala-Ala-Leu-Ala (SEQ ID NO: 2); and Glu-Gly-Glu-Gly-Leu-Ala-Leu-Leu-Ala-His-Ala-Leu-Leu-Ala-His-Ala-Ala-Leu-Ala-His-Ala-Ala-Leu-Ala (SEQ ID NO: 3).

The peptide compound of the present invention essentially comprises the above-mentioned hydrophilic amino acid block and hydrophobic amino acid block. Peptide compounds comprising only hydrophobic amino acid blocks are not considered to induce a structural change of liposomes for the following reason. That is, such peptide compounds are taken up by the hydrophobic region of liposomes, and protons cannot enter the liposomes; therefore, the peptide compounds do not respond even when the surrounding environment is acidified. Comparatively, peptide compounds comprising only hydrophilic amino acid blocks cannot be incorporated into liposomes.

The peptide compound of the present invention may have a C-terminal protecting group at the C-terminus. The C-terminal protecting group includes a group that forms an amide with the carbon atom of the C-terminal carboxyl group, or a group that forms an ester with the oxygen atom of the carboxyl group. Examples of the group that forms an ester include alkyl groups, in particular $C_1$-$C_5$ linear or branched alkyl groups ($C_1$-$C_5$ alkyl groups), such as methyl, ethyl, and propyl. Examples of the group that forms an amide include amine functional groups, such as amino; and alkyl amino functional groups, such as methylamino, ethylamino, dimethylamino, diethylamino, methylethylamino, and other mono- or di-$C_1$-$C_5$ alkylamino groups. The group that forms an amide is preferable; amino is more preferable.

The peptide compound of the present invention can be produced by a known peptide synthesis method, in particular, a liquid-phase synthesis method or a solid-phase synthesis method. It is also possible to synthesize the peptide compound of the present invention by a method comprising introducing DNA encoding the peptide compound of the present invention into a host cell, and expressing the DNA, using a gene recombination technique. For example, in solid-phase synthesis, the peptide compound of the present invention can be obtained as follows: the carboxyl group of an N-protected amino acid, in which the amino group of the amino acid corresponding to the C-terminus is protected with a urethane protecting group such as 9-fluorenylmethyloxycarbonyl (Fmoc) group, is bonded to an insoluble resin having amino groups; the protecting group of the amino group is then removed to successively condense protected amino acids in the N-terminal direction; and the insoluble resin and the protecting groups of amino acids are removed to thereby obtain the peptide compound of the present invention. The above-mentioned insoluble resin having amino groups is not particularly limited, but is preferably an Fmoc-NH-SAL resin (4-(2',4'-dimethoxyphenyl-Fmoc-aminoethyl)phenoxy linker resin); a target substance can be directly given thereto by resin cleavage. The protected amino acid used in synthesis of the peptide compound of the present invention can be obtained by protecting a functional group with a known protecting group by using a known method. It is also possible to use commercially available protected amino acids. As a protecting group, known protecting groups can be used. Examples thereof include methoxycarbonyl, ethoxycarbonyl, tert-butoxycarbonyl, 9-fluorenylmethoxycarbonyl, benzyloxycarbonyl, 4-methoxybenzyloxycarbonyl, 2,2,2-trichloroethyloxycarbonyl, formyl, acetyl, propionyl, butyryl, and the like. To prepare protected amino acids, for example, known methods can be used, such as a DIPCDI-HOBt (diisopropylcarbodiimide-1-hydroxybenzotriazole) method. This condensation reaction can be performed in a known solvent, e.g., an organic solvent such as dimethylformamide. The deprotection reagent for amino-protecting groups is not limited, and a known reagent, such as piperidine/dimethylformamide, can be used to cleave a protecting group such as Fmoc. Deprotection of a urethane protecting group can be performed, for example, by catalytic reduction or with the use of trifluoroacetic acid. Deprotection of other protecting groups can also be performed by a known method. The degree of progress of the condensation reaction in each synthetic step can be confirmed by a known method, such as a ninhydrin reaction method. As such, a protected peptide having a desired amino acid sequence can be obtained. The use of an Fmoc-NH-SAL resin as the insoluble resin can simultaneously remove the resin and protecting group by a treatment with TMSBr (trimethylsilylbromide), TFA (trifluoroacetic acid), or the like. The peptide compound can be obtained with the C-terminus of COOH or CONH$_2$, depending on the type of the resin used.

The thus-obtained peptide compound of the present invention can be isolated and purified by a known means, such as extraction, recrystallization, a variety of chromatography methods (gel filtration, ion exchange, partition, and adsorption), electrophoresis, and countercurrent distribution. A reversed-phase high-pressure liquid chromatography method is preferable.

As long as the liposome of the present invention is a closed vesicle with a lipid bilayer structure, it may be a multilamellar liposome (MLV), or a unilamellar liposome, such as SUV (small unilamellar vesicle), LUV (large unilamellar vesicle), or GUV (giant unilamellar vesicle).

Specific examples of the type of lipid that forms a lipid bilayer in the liposome of the present invention include, but are not limited to, phosphatidylcholines (e.g., dioleoylphosphatidylcholine, dilauroylphosphatidylcholine, dimyristoylphosphatidylcholine, dipalmitoylphosphatidylcholine, and distearoylphosphatidylcholine), phosphatidylglycerols (e.g., dioleoylphosphatidylglycerol, dilauroylphosphatidylglycerol, dimyristoylphosphatidylglycerol, dipalmitoylphosphatidylglycerol, and distearoylphosphatidylglycerol (DSPG)), phosphatidylethanolamine (e.g., dioleoylphosphatidylethanolamine, dilauroylphosphatidylethanolamine, dimyristoylphosphatidylethanolamine, dipalmitoylphosphatidylethanolamine, and distearoylphosphatidylethanolamine), phosphatidylserine, phosphatidylinositol, phosphatidic acid, cardiolipin, and like phospholipids or hydrogen additives thereof; and sphingomyelin, ganglioside, and like glycolipids. These may be used singly or in a combination of two or more. Phospholipids may be synthetic lipids, semi-synthetic lipids, or natural lipids derived from egg yolk, soybean, or other animals or plants (e.g., egg yolk lecithin and soybean lecithin). These lipids may be used singly or in a combination of two or more.

To achieve physical or chemical stabilization of the lipid bilayer, and to adjust the membrane fluidity, the lipid bilayer may comprise one or more members selected from, for example, cholesterol, cholesterol succinic acid, lanosterol, dihydrolanosterol, desmosterol, dihydrocholesterol, and like animal-derived sterols; stigmasterol, sitosterol, campesterol, brassicasterol, and like plant-derived sterols (phytosterols); zymosterol, ergosterol, and like microorganism-derived sterols; glycerol, sucrose, and like saccharides; and triolein, trioctanoin, and like glycerine fatty acid esters. The amount thereof is not particularly limited, but is preferably 5 to 40% (molar ratio), and more preferably 10 to 30% (molar ratio), based on the total amount of the lipids constituting the bilayer.

The lipid bilayer may comprise tocopherol, propyl gallate, ascorbyl palmitate, butylated hydroxytoluene, and like antioxidant agents; stearylamine, oleylamine, and like charged materials for providing a positive charge; dicetyl phosphate and like charged materials for providing a negative charge; and membrane extrinsic protein, membrane intrinsic protein, and like membrane proteins. The amount thereof can be suitably adjusted.

It is more preferable that the liposome of the present invention contains a cationic lipid (cationic liposome). Examples of cationic lipids include DODAC (dioctadecyldimethylammonium chloride), DOTMA (N-(2,3-dioleyloxyl)propyl-N,N,N-trimethylammonium), DDAB (didodecylammonium bromide), DOTAP (1,2-dioleoyloxy-3-trimethylammonio propane), DC-Chol (3β-N—(N',N',-dimethyl-aminoethane)-carbamol cholesterol), DMRIE (1,2-dimyristoyloxypropyl-3-dimethylhydroxyethyl ammonium), DOSPA (2,3-dioleyloxy-N-[2(sperminecarboxamido)ethyl]-N,N-dimethyl-1-propanaminum trifluoroacetate), DSTAP (1,2-distearoyl-3-trimethylammonium propane), DODAP (dioleoyl-3-dimethylammonium-propane), and the like. A preferred cationic lipid is DOTMA, DSTAP, or DODAP; and a particularly preferred cationic lipid is DOTAP. Cationic lipids can be used singly or in a mixture of two or more.

Of cationic lipids, DOTMA and DSTAP have a quaternary amine and always have a positive charge, whereas DODAP has a tertiary amine and does not have a charge at a physiological pH. Cationic lipids can thus have various structures and characteristics by changing the type and amount of cationic lipids.

The liposome of the present invention preferably comprises an auxiliary lipid (helper lipid). Examples of auxiliary lipids include EPC (egg phosphatidylcholine), DLPC (dilinoleoylphosphatidylcholine), DMPC (dimyristoylphosphatidylcholine), DPPC (dipalmitoylphosphatidylcholine), DSPC (distearoylphosphatidylcholine), POPC (palmitoyloleoylphosphatidylcholine), DOPC (dioleoylphosphatidylcholine), DOPE (dioleoylphosphatidylethanolamine), SOPE (stearyloleoylphosphatidylcholine), and the like. Of these, EPC, DOPC, DOPE, and SOPE are preferable.

The liposome of the present invention has the peptide compound of the present invention as a constituent component. When the peptide compound of the present invention is used, it is preferable to add it in an amount of about 1 to 10 mol % based on 100 mol % of the lipids constituting the liposome.

The liposome of the present invention can be modified with a hydrophilic polymer.

Examples of hydrophilic polymers include polyalkylene glycols (polyalkylene glycol copolymers, such as block copolymers of polypropylene glycol and polyethylene glycol, polypropylene glycol, polybutylene glycol, or polyethylene glycol), dextran, pullulan, Ficoll, polyvinyl alcohol, styrene-maleic acid anhydride-alternating copolymers, divinyl ether-maleic acid anhydride-alternating copolymers, amylose, amylopectin, chitosan, mannan, cyclodextrin, pectin, carrageenan, and the like; preferably polyalkylene glycols (polyalkylene glycol copolymers, such as block copolymers of polypropylene glycol and polyethylene glycol, polypropylene glycol, polybutylene glycol, or polyethylene glycol); and particularly preferably polyethylene glycol (PEG). It is preferable to modify the liposome with such a hydrophilic polymer. Examples of PEG include DSPE (distearoyl phosphatidylethanolamine)-PEG2000, DMPE (dimyristoyl phosphatidylethanolamine)-PEG2000, DSG (distearoylglycerol)-PEG2000, DMG (dimyristoylglycerol)-PEG2000, cholesterol PEG2000, stearyl PEG2000, C8 ceramide PEG2000, C16 ceramide PEG2000, and the like. Of these, stearyl PEG2000 or C8 ceramide PEG2000 is preferable. The length of PEG can be suitably selected within a molecular weight range of about 500 to 10,000. A person skilled in the art can also suitably select the molecular weight of other hydrophilic polymers in the same manner.

For example, when liposomes are PEG-modified, it is preferable to use stearylated PEG (STR-PEG), C8 ceramide PEG, or cholesterol-PEG, in order to impart excellent storage stability to the liposomes, without impairing functional expression of a target substance (e.g., a nucleic acid drug, such as siRNA). It is also preferable to use DSPE-PEG, DSG-PEG, C16 ceramide-PEG, or the like, in order to improve blood stability. When liposomes are modified with a hydrophilic polymer, it is preferable to modify the liposomes with the hydrophilic polymer in an amount of about 1 to 15 mol % based on 100 mol % of the lipids constituting the liposome.

The liposome of the present invention can be produced by using a known method, such as a hydration method, ultrasonication method, ethanol injection method, ether injection method, reverse-phase evaporation method, freezing and thawing method, or the like.

A production example of liposomes using a hydration method is described below.

Lipids, which are a constituent component of a lipid bilayer, and the peptide compound of the present invention are dissolved in an organic solvent, followed by removal of the organic solvent by evaporation, thereby obtaining a lipid membrane. Examples of the organic solvent used herein include hydrocarbons, such as pentane, hexane, heptane, and cyclohexane; halogenated hydrocarbons, such as methylene chloride and chloroform; aromatic hydrocarbons, such as benzene and toluene; lower alcohols, such as methanol and ethanol; esters, such as methyl acetate and ethyl acetate; ketones, such as acetone; and the like. These may be used singly or in a combination of two or more. Subsequently, the lipid membrane is hydrated, and stirred or ultrasonicated, thereby producing liposomes having the peptide compound of the present invention.

Further, another production example of liposomes using a hydration method is described below.

Lipids, which are a constituent component of a lipid bilayer, are dissolved in an organic solvent, followed by removal of the organic solvent by evaporation, thereby obtaining a lipid membrane. This lipid membrane is hydrated, and stirred or ultrasonicated to produce liposomes. Subsequently, the peptide compound of the present invention is added to the external liquid of the liposomes. The peptide compound of the present invention can thereby be introduced into the liposomes.

For example, the preparation of liposomes using a quaternary amine as the cationic lipid can be performed by the same method as in Example 4, described later, a similar method, or a combination of such methods and a standard method. Moreover, the preparation of liposomes using a tertiary amine as the cationic lipid can be performed by the same method as in Example 4, described later, a similar method, or a combination of such methods and a standard method.

In the preparation of liposomes, the ratio of auxiliary lipid (EtOH solution)/cationic lipid (EtOH solution) can be suitably changed.

Preferred examples of the liposome of the present invention include liposomes having the composition of EPC/DOTAP/the peptide compound of present invention, EPC/the peptide compound of the present invention, or EPC/DSPG/the peptide compound of the present invention; and more preferably liposomes having the composition of EPC/DOTAP/the peptide compound of the present invention.

The liposome of the present invention has a zeta potential of about −50 to +50 mV, preferably about −40 to +40 mV, and more preferably about −30 to +30 mV, at about a neutral pH (e.g., pH 7 or 7.4). Zeta potential can be measured by using a Zetasizer.

The liposomes of the present invention have an average particle diameter of, for example, 30 to 1,000 nm, preferably 50 to 500 nm, and more preferably 60 to 200 nm, although it is not limited thereto. The average particle diameter can be measured, for example, by a dynamic light-scattering method, a static light-scattering method, electron microscope observation, atomic force microscope observation, or the like.

A target substance to be delivered into a cell can be encapsulated in the liposome of the present invention.

When the target substance is water-soluble, it is added to an aqueous solvent that is used when a lipid membrane is hydrated during the production of liposomes. The target substance can thereby be encapsulated in the aqueous phase of the liposomes. When liposoluble, the target substance is added to the organic solvent used during the production of liposomes; the target substance can thereby be encapsulated in the lipid bilayer of the liposomes. The term "encapsulate" as used in the present specification indicates the case where a target substance is included inside a hollow particle such as a liposome.

The organism species to which a target substance is delivered is not limited as long as they are vertebrate animals. Mammals are preferable. Examples of mammals include humans, apes, cows, sheep, goats, horses, pigs, rabbits, dogs, cats, rats, mice, guinea pigs, and the like.

The liposome of the present invention may be used in a dispersion state. As a dispersion solvent, a buffer solution such as a physiological saline solution, a phosphate buffer solution, a citrate buffer solution, or an acetic acid buffer solution can be used. Additives, such as a saccharide, a polyhydric alcohol, a water-soluble polymer, a non-ionic surfactant, an antioxidant agent, a pH regulator, and a hydration accelerator, may be added to the dispersion.

The liposome of the present invention may also be used in a dried dispersion state (e.g., freeze-dried or spray-dried). The dried liposomes may be added to a buffer solution, such as a physiological saline solution, a phosphate buffer solution, a citrate buffer solution, or an acetate buffer solution, to prepare a dispersion.

The liposome of the present invention may be used both in vitro and in vivo. When the liposome of the present invention is used as a pharmaceutical composition, the administration route may be, for example, intravenous injection, intravenous drip, or the like. The dosage and administration frequency can be suitably adjusted according to the type and amount of the target substance encapsulated in the liposome of the present invention.

When used as a pharmaceutical composition, the liposome of the present invention may contain a pharmaceutical carrier, if necessary. Various dosage forms can be used according to the purpose, such as diagnosis or treatment. For example, injections can be used as dosage forms. Various dosage forms can be produced by known preparation methods commonly used by a person skilled in the art.

When injections are prepared, a pH regulator, buffer, stabilizing agent, isotonic agent, etc., can be added to a target substance. Subcutaneous, intramuscular, and intravenous injections can be produced by standard methods.

Examples of pH regulators and buffers include sodium citrate, sodium acetate, sodium phosphate, and the like. Examples of stabilizing agents include sodium pyrosulfite, EDTA, thioglycolic acid, thiolactic acid, and the like. Examples of isotonic agents include sodium chloride, glucose, D-mannitol, glycerol, and the like.

The liposome of the present invention causes neither weight loss nor hepatopathy, and can therefore be administered safely.

The substance induction agent of the present invention can be used either in vitro or in vivo to deliver a target substance to a weakly acidic pH site. Examples of weakly acidic pH sites include inflammation sites, tumor sites, infected sites, and the like. In particular, tumor sites are preferable.

Examples of the target substance to be encapsulated include, but are not particularly limited to, one or more members selected from the group consisting of drugs, nucleic acids, peptides (e.g., oxytocin, bradykinin, thyrotropin-releasing factor, enkephalin, and like biologically active peptides and peptide hormones), proteins (e.g., enzyme, interleukin and various like cytokines, cell transfer factor, cell growth factor, and antibodies), sugar, and composites thereof. These can be selected according to the purpose, such as diagnosis or treatment. Nucleic acids include DNA and RNA, as well as analogues and derivatives of DNA and RNA (e.g., siRNA, peptide nucleic acid (PNA), and phosphorothioate DNA). Nucleic acids can either be single- or double-stranded, and can either be linear or circular nucleic acids.

Furthermore, the liposome of the present invention can be designed to release, in different sites, several types of target substances having different molecular weights encapsulated in the same liposome. For example, the liposome of the present invention can be designed to release a low-molecular substance with a molecular weight of 700 or less in a weakly acidic pH-specific manner, and not to release a high-molecular substance with a molecular weight of 700 or more in a weakly acidic pH environment, but to release it after the liposome is uptake into a tumor cell.

The target substance is contained in an amount of 0.1 to 60 parts by mass, and preferably 1 to 40 parts by mass, based on 100 parts by mass in total of the peptide and the lipids constituting the liposome.

When the target substance is a drug, any drugs that are used in tissue in a weakly acidic environment (pH around 6.5) can be used. For example, anticancer agents can be used. Specific examples of anticancer drugs include tegafur, doxorubicin, daunorubicin, cis-platinum, oxaliplatin, carboplatin, paclitaxel, irinotecan, SN-38, actinomycin D, vincristine, vinblastine, methotrexate, azathioprine, fluorouracil, mitomycin C, docetaxel, cyclophosphamide, capecitabine, epirubicin, gemcitabine, mitoxantrone, leucovorin, vinorelbine, trastuzumab, etoposide, estramustine, prednisone, interferon α, interleukin-2, bleomycin, ifosfamide, mesna, altretamine, topotecan, cytarabine, methyl- prednisolone, dexamethasone, mercaptopurine, thioguanine, fludarabine, gemtuzumab, idarubicin, mitoxantrone, tretinoin, alemtuzumab, chlorambucil, cladribine, imatinib, epirubicin, dacarbazine, procarbazine, mechlorethamine, rituximab, denileukin diftitox, trimethoprim/sulfamethoxazole, allopurinol, carmustine, tamoxifen, filgrastim, temozolomide, melphalan, vinorelbine, azacitidine, thalidomide, mitomycin, and the like. Furthermore, anti-inflammatory agents can also be used as a target substance because inflammatory sites are also weakly acidic regions. Examples of anti-inflammatory agents include non-steroidal anti-inflammatory agents (e.g., ibuprofen, ketoprofen, naproxen, indomethacin, aspirin, diclofenac, piroxicam, acetaminophen, celecoxib, and rofecoxib) and steroidal anti-inflammatory agents (e.g., hydrocortisone, prednisolone, dexamethasone, and betamethasone).

Preferable examples of nucleic acids used as the target substance include any of double-stranded RNAs (dsRNAs) selected from the group consisting of meroduplex RNA (mdRNA), nicked dsRNA (ndsRNA), gapped dsRNA (gdsRNA), short interfering nucleic acid (siNA), siRNA, microRNA (miRNA), short hairpin RNA (shRNA), short interfering oligonucleotide, short interfering substituted oligonucleotide, short interfering modified oligonucleotide, chemically modified dsRNA, and post-transcriptional gene-silencing RNA (ptgsRNA). The target substance may be used singly or in a combination of two or more. For example, two or more types of siRNAs may be used in combination.

In one embodiment in terms of substitution and modification (including chemical modification), a double-stranded RNA may comprise an overhang of one to four nucleotides at one or both 3' ends of the double-stranded RNA, such as an overhang comprising a deoxyribonucleotide or two deoxyribonucleotides (e.g., thymidine, adenine). A double-stranded RNA may have a blunt end at one or both ends of the double-stranded RNA. In one embodiment, the 5' end of the first or second strand is phosphorylated. In any of the embodiments of double-stranded RNA, the nucleotide overhangs at the 3' end can comprise ribonucleotides or deoxyribonucleotides that are chemically modified at a nucleic acid sugar, base, or backbone. In any of the embodiments of double-stranded RNA, the nucleotide overhangs at the 3' end can comprise one or more universal base ribonucleotides. In any of the embodiments of double-stranded RNA, the nucleotide overhangs at the 3' end can comprise one or more acyclic nucleotides. In any of the embodiments of double-stranded RNA, dsRNA can further comprise a terminal phosphate group, such as a 5'-phosphate (see Martinez et al., Cell, 110: 563-574, 2002; and Schwarz et al., Molec. Cell, 10: 537-568, 2002) or a 5',3'-diphosphate.

A double-stranded RNA can further comprise a 2'-sugar substitution, such as 2'-deoxy, 2'-O-methyl, 2'-O-methoxyethyl, 2'-O-2-methoxyethyl, halogen, 2'-fluoro, or 2'-O-allyl, or a combination thereof. In further embodiments, a double-stranded RNA further comprises a terminal cap substituent on one or both ends of the first strand or one or more of the second strands, such as an alkyl, abasic, deoxy abasic, glyceryl, dinucleotide, acyclic nucleotide, inverted deoxynucleotide moiety, or a combination thereof.

In further embodiments, a double-stranded RNA may further comprise at least one modified internucleoside linkage, such as independently a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, boranophosphate linkage, or a combination thereof.

A double-stranded RNA can be substituted or modified (including chemical modification) by using 5-methylcytosine; 5-hydroxymethyl cytosine; xanthine; hypoxanthine; 2-aminoadenine; 6-methyl, 2-propyl, or other alkyl derivatives of adenine and guanine; 8-substituted adenines and guanines (e.g., 8-aza, 8-halo, 8-amino, 8-thiol, 8-thioalkyl, 8-hydroxyl); 7-methyl, 7-deaza, and 3-deaza adenines and guanines; 2-thiouracil; 2-thiothymine; 2-thiocytosine; 5-methyl, 5-propynyl, 5-halo (e.g., 5-bromo or 5-fluoro), 5-trifluoromethyl, or other 5-substituted uracils and cytosines; and nucleotide analogues, such as 6-azouracil.

RNAs, such as double-stranded RNAs (dsRNAs), may be chemically modified. Examples of such chemical modifications include, but are not limited to, phosphorothioate internucleotide linkages, 2'-deoxyribonucleotides, 2'-O-methyl ribonucleotides, 2'-deoxy-2'-fluoro ribonucleotides, "acyclic" nucleotides, 5'-C-methyl nucleotides, and terminal glyceryl and/or inverted deoxy abasic residue incorporation. These chemical modifications can preserve RNAi activity in cells.

The present invention provides a pharmaceutical composition comprising the above liposome. Target diseases to be prevented or treated by the pharmaceutical composition of the present invention can be selected depending on the type of target substance, and are not particularly limited. Examples of the pharmaceutical composition of the present invention include antitumor agents, and the like.

In this embodiment, the target cancer is not particularly limited. Examples thereof include head and neck cancer, esophageal cancer, stomach cancer, colon cancer, rectal cancer, liver cancer, gallbladder and bile duct cancer, biliary tract cancer, pancreatic cancer, lung cancer, breast cancer, ovarian cancer, cervical cancer, endometrial cancer, renal cancer, vesical cancer, prostatic cancer, testicular tumor, bone and soft-tissue sarcoma, multiple myeloma, skin cancer, brain tumor, mesothelioma, melanoma, and the like.

EXAMPLES

The present invention is described below in more detail with reference to Examples and Test Examples. However, the scope of the present invention is not limited to these Examples.

Example 1

Synthesis of HGHGLALLAHALLAHAALAHAALA (SEQ ID NO: 1, Peptide Compound 1)

Using a Fmoc-Ala-HMP resin as a starting material, with a scale of 0.1 mM, the peptide of SEQ ID NO: 1 was synthesized by Fmoc solid-phase synthesis using amino acids, a condensation agent (HBTU/HOBt), and a reaction accelerator (DIEA) (4 equivalents each relative to the resin). (HBTU: M.W. 379.2, HOBt, Anhydrous: M.W. 135.1, DIEA: M.W. 129.2). A TFA (trifluoroacetic acid) cocktail solution (TFA: 125 mL; $H_2O$: 0.25 mL; phenol: 0.375 g; ethanedithiol: 0.125 mL; and thioanisole: 0.25 mL) was added to the synthesized resin and reacted under ice-cooling for 15 minutes, and at room temperature for 2 hours. A peptide was cleaved from the resin, and precipitated in diethyl ether to obtain a crude peptide. Purification was performed by HPLC, followed by lyophilization. Purity was measured by HPLC and MALDI-TOF-MS. Analysis was performed under the following HPLC conditions, and the target peptide compound 1 (SEQ ID NO: 1) was obtained as a single peak. The average hydropathy index was shown in Table 3, provided later.

A Buffer: 0.1% TFA/$H_2O$; B Buffer: 0.1% TFA/acetonitrile; Column: SunFire C18 Column, 5 μm, 4.6×150 mm; Flow rate: 1 mL/min; Wavelength: 220 nm.

Figure 1B:
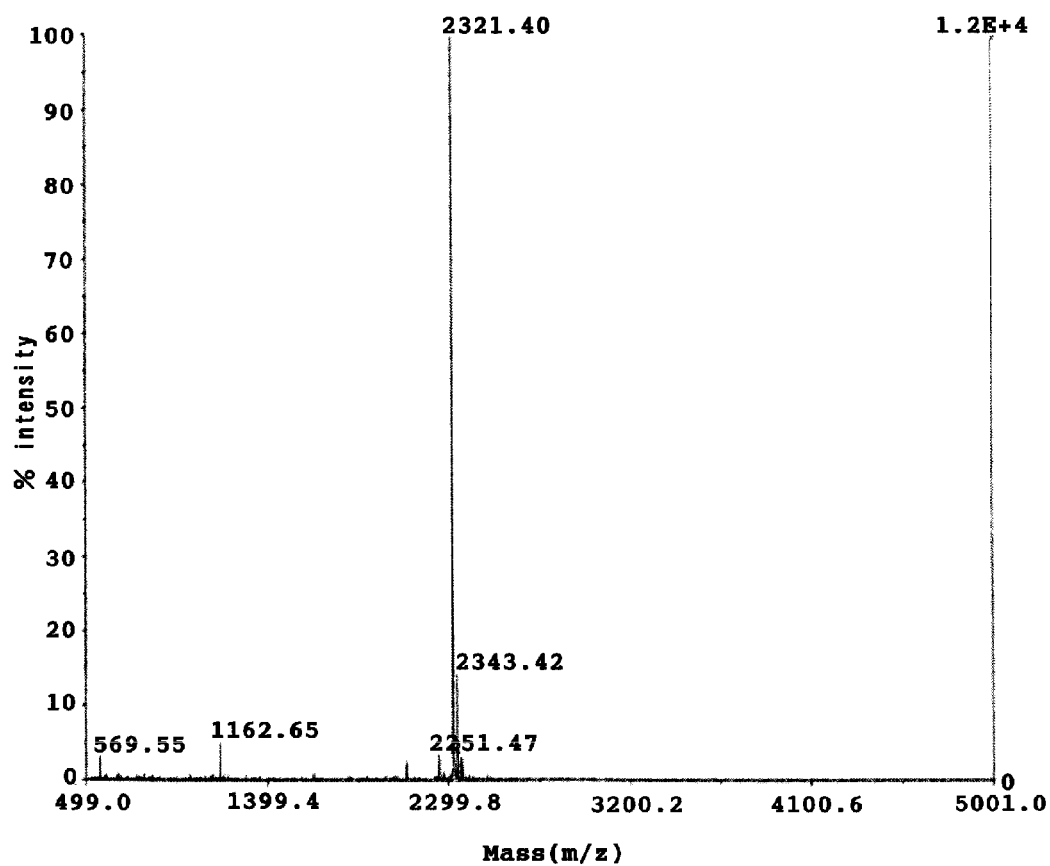
FIG. 1B shows the MALDI-TOF-MS results of peptide compound 1 (SEQ ID NO: 1) obtained in Example 1.

An Applied Biosystems Voyager System was used for MALDI-TOF-MS. Molecular weight calcd.: 2320.7. found: 2321.40. FIG. 1 shows the results of HPLC and MALDI-TOF-MS.

Synthesis scale: a 0.1-mM scale (molecular weight: 2020.7);
Resin used: Fmoc-Ala-HMP resin;
Amount of resin used: 208.0 mg (amount of resin introduced: 0.48 mmol/g);
Theoretical value of the peptide obtained by using this resin: 232.3 mg;
Crude amount actually obtained: 228.6 mg (yield: 98.4%).

Example 2

Synthesis of GHHGLALLHALHLAAAALHAAALA (Peptide Compound 2)

Figure 2A:
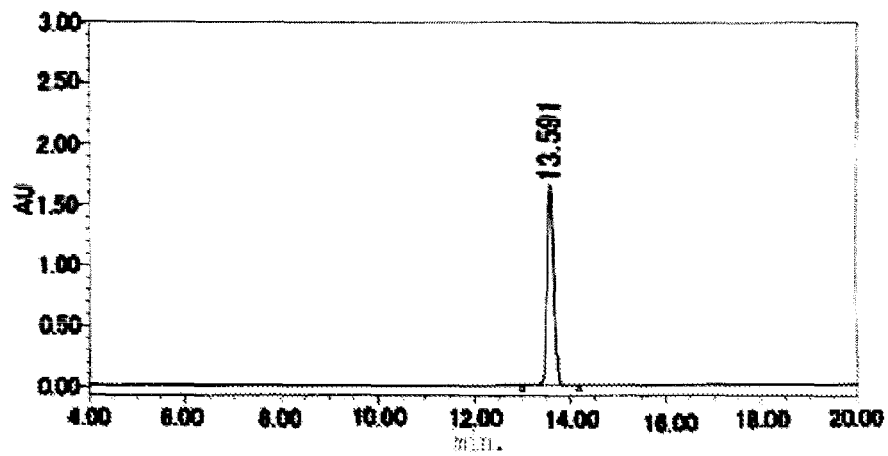
FIG. 2A shows the HPLC results of peptide compound 2 (SEQ ID NO: 2) obtained in Example 2.
Figure 2B:
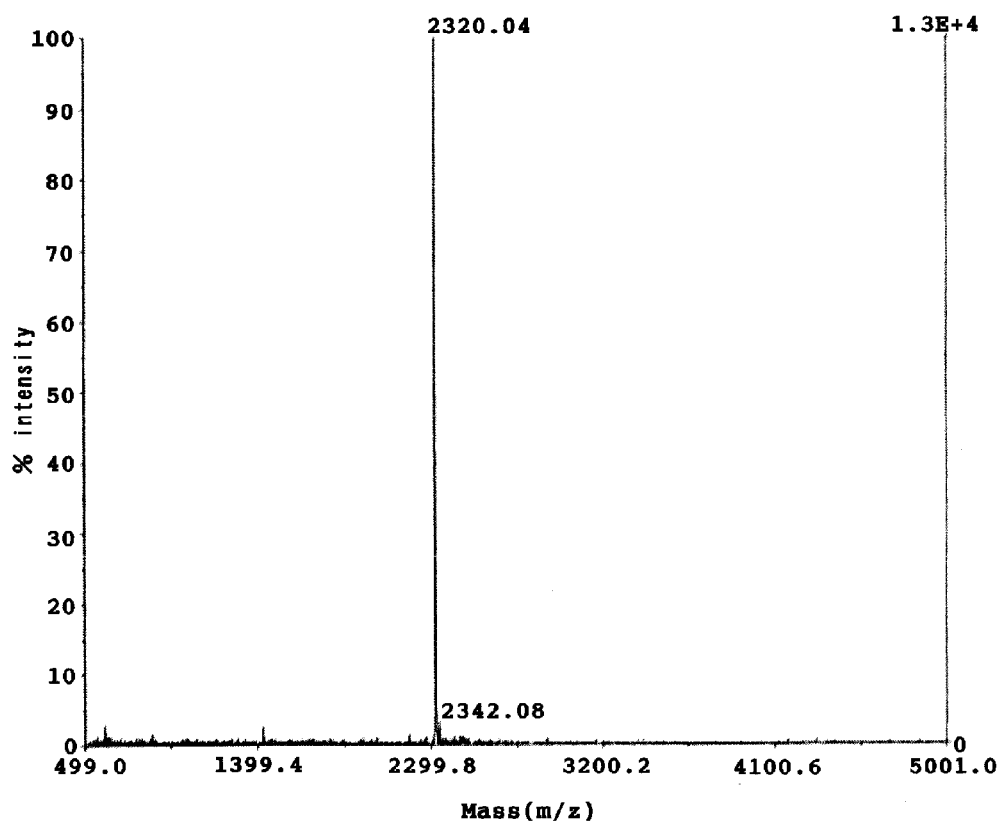
FIG. 2B shows the MALDI-TOF-MS results of peptide compound 2 (SEQ ID NO: 2) obtained in Example 2.

Synthesis was performed as in Example 1 to obtain peptide compound 2 (SEQ ID NO: 2). Molecular weight calcd.: 2320.7. found: 2320.04. FIG. 2 shows the results of HPLC and MALDI-TOF-MS. The average hydropathy index was shown in Table 3, provided later.

Synthesis scale: a 0.1-mM scale (molecular weight: 2320.7);
Resin used: Fmoc-Ala-HMP resin;
Amount of resin used: 140.1 mg (amount of resin introduced: 0.72 mmol/g);
Theoretical value of the peptide obtained by using this resin: 234.0 mg;
Crude amount actually obtained: 95.5 mg (yield: 40.8%)

Example 3

Synthesis of EGEGLALLAHALLAHAALAHAALA (Peptide Compound 3)

Figure 3A:
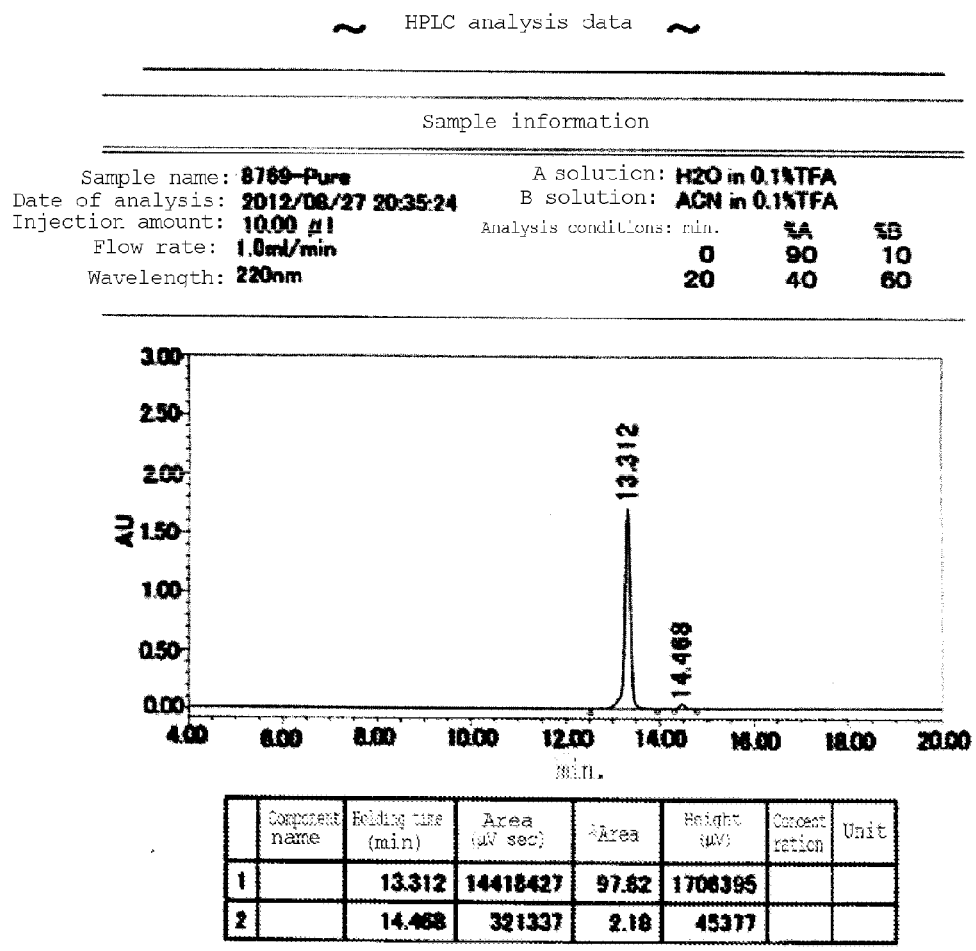
FIG. 3A shows the HPLC results of peptide compound 3 (SEQ ID NO: 3) obtained in Example 3.
Figure 3B:
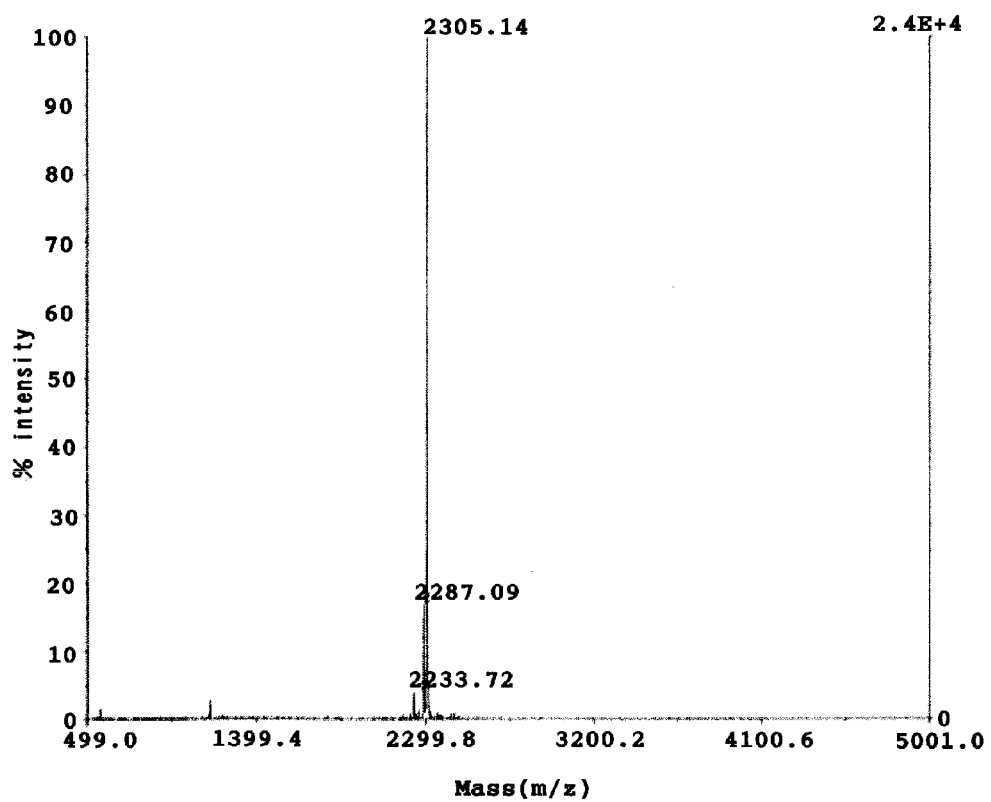
FIG. 3B shows the MALDI-TOF-MS results of peptide compound 3 (SEQ ID NO: 3) obtained in Example 3.

Synthesis was performed as in Example 1 to obtain peptide compound 3 (SEQ ID NO: 3). Molecular weight calcd.: 2304.6. found: 2305.14. FIG. 3 shows the results of HPLC and MALDI-TOF-MS. The average hydropathy index was shown in Table 3, provided later.

Synthesis scale: a 0.1-mM scale (molecular weight: 2304.6);
Resin used: Fmoc-Ala-HMP resin;
Amount of resin used: 175.6 mg (amount of resin introduced: 0.60 mmol/g);
Theoretical value of the peptide obtained by using this resin: 242.7 mg;
Crude amount actually obtained: 240.1 mg (yield: 98.9%).

Comparative Example 1

Synthesis of HHGGLLLLHHHAAAAALLLAAAAA (Comparative Compound 1)

Figure 4A:
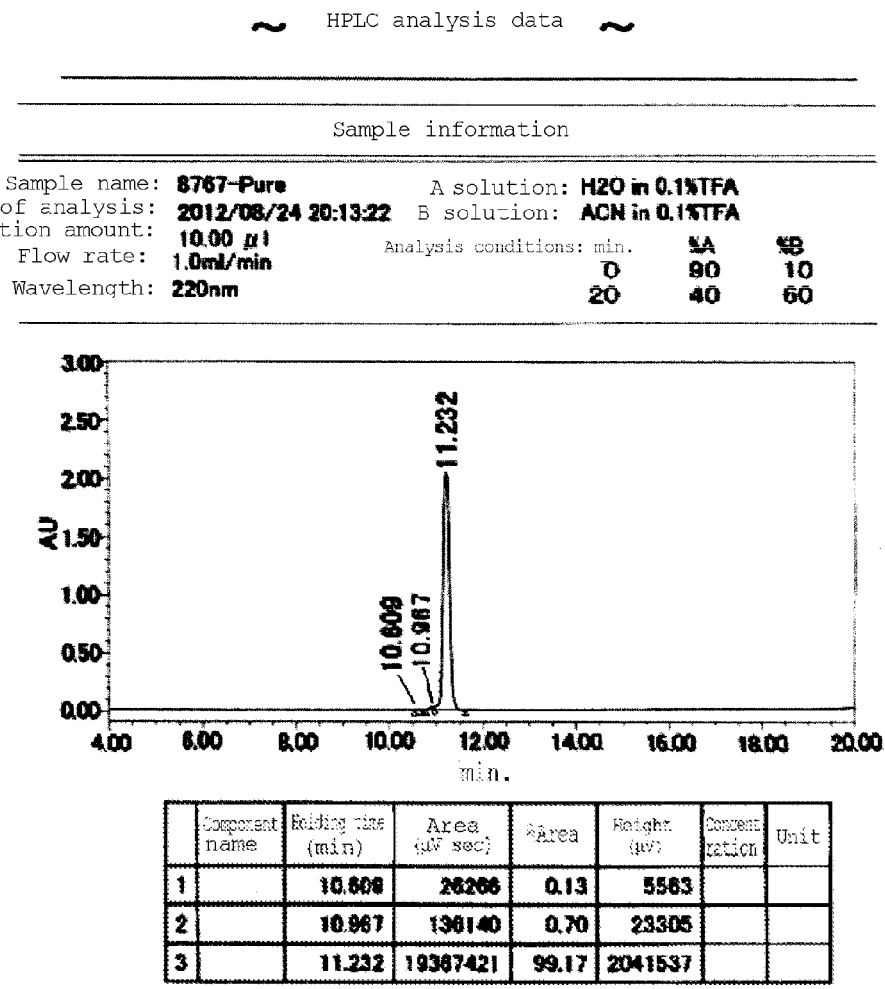
FIG. 4A shows the HPLC results of comparative compound 1 (SEQ ID NO: 4) obtained in Comparative Example 1.
Figure 4B:
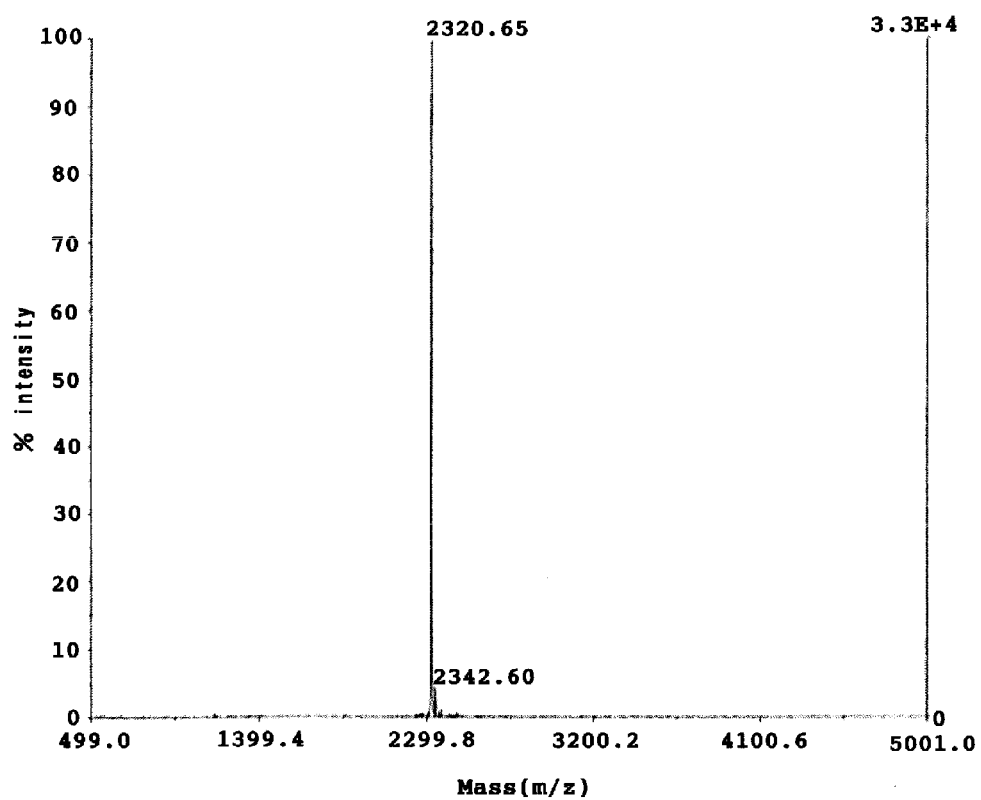
FIG. 4B shows the MALDI-TOF-MS results of comparative compound 1 (SEQ ID NO: 4) obtained in Comparative Example 1.

Synthesis was performed as in Example 1 to obtain comparative compound 1 (SEQ ID NO: 4). Molecular weight calcd.: 2320.7. found: 2320.65. FIG. 4 shows the results of HPLC and MALDI-TOF-MS. The average hydropathy index was shown in Table 3, provided later.
Synthesis scale: a 0.1-mM scale (molecular weight: 2320.7);
Resin used: Fmoc-Ala-HMP resin;
Amount of resin used: 179.8 mg (amount of resin introduced: 0.58 mmol/g);
Theoretical value of the peptide obtained by using this resin: 242.0 mg;
Crude amount actually obtained: 233.4 mg (yield 96.4%).

Comparative Example 2

Synthesis of HGHGGGGGGGGGAHALLAHAALAH (Comparative Compound 2)

Figure 5A:
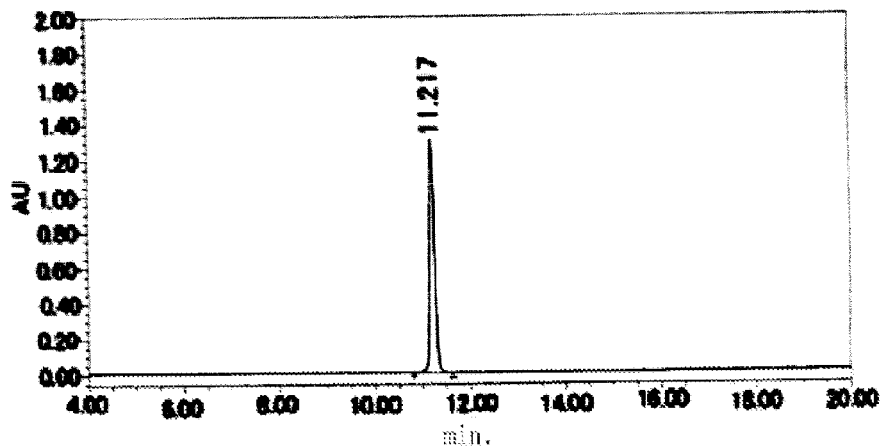
FIG. 5A shows the HPLC results of comparative compound 2 (SEQ ID NO: 5) obtained in Comparative Example 2.
Figure 5B:
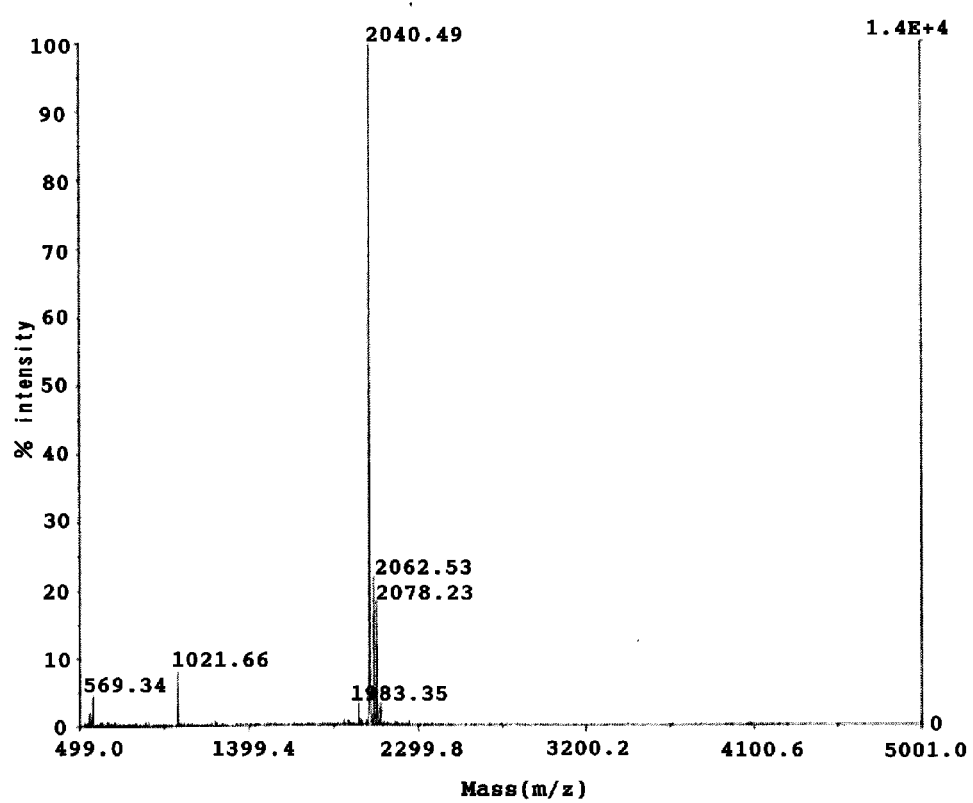
FIG. 5B shows the MALDI-TOF-MS results of comparative compound 2 (SEQ ID NO: 5) obtained in Comparative Example 2.

Synthesis was performed as in Example 1 to obtain comparative compound 2 (SEQ ID NO: 5). Molecular weight calcd.: 2040.1. found: 2040.49. FIG. 5 shows the results of HPLC and MALDI-TOF-MS. The average hydropathy index was shown in Table 3, provided later.
Synthesis scale: a 0.1-mM scale (molecular weight: 2040.1);
Resin used: H-His(Trt)-Trt(2-Cl)-resin;
Amount of resin used: 217.6 mg (amount of resin introduced: 0.50 mmol/g);
Theoretical value of the peptide obtained by using this resin: 222.0 mg;
Crude amount actually obtained: 182.9 mg (yield: 82.4%).

Comparative Example 3

Synthesis of HGHGLALLAHALLAHAAAAL (Comparative Compound 3)

Figure 6A:
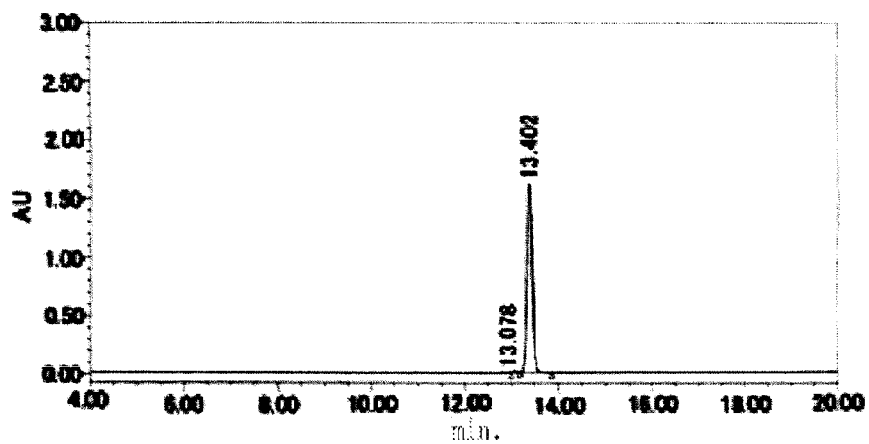
FIG. 6A shows the HPLC results of comparative compound 3 (SEQ ID NO: 6) obtained in Comparative Example 3.
Figure 6B:
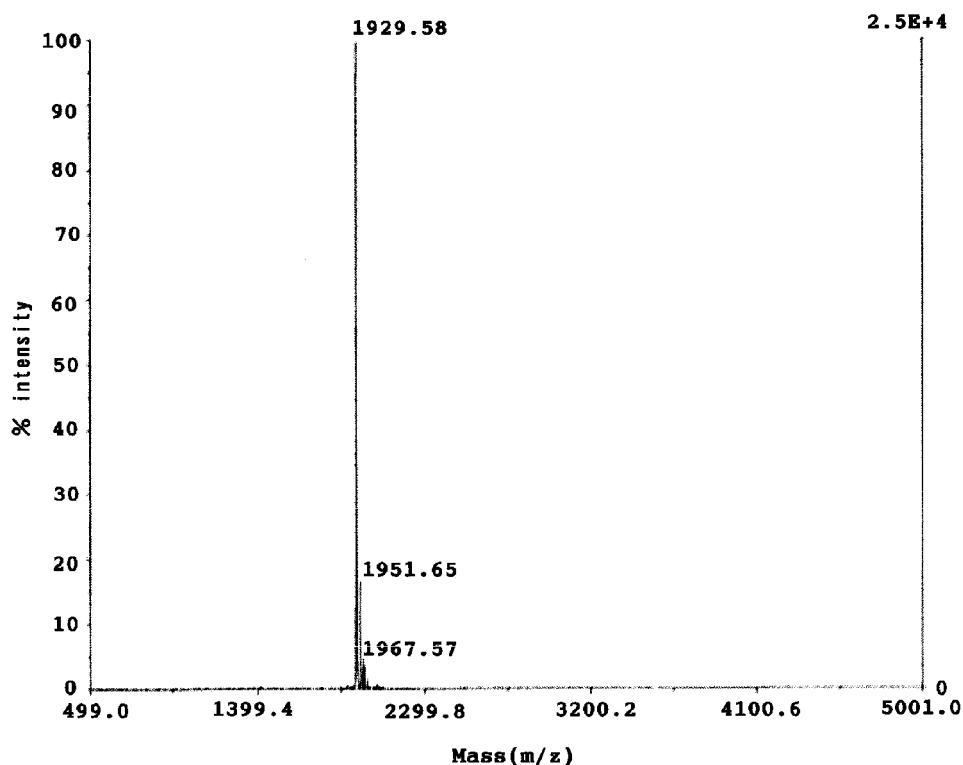
FIG. 6B shows the MALDI-TOF-MS results of comparative compound 3 (SEQ ID NO: 6) obtained in Comparative Example 3.

Synthesis was performed as in Example 1 to obtain comparative compound 3 (SEQ ID NO: 6). Molecular weight calcd.: 1928.2. found: 1929.58. FIG. 6 shows the results of HPLC and MALDI-TOF-MS. The average hydropathy index was shown in Table 3, provided later.
Synthesis scale: a 0.1-mM scale (molecular weight: 1928.2);
Resin used: Fmoc-Leu-HMP resin;
Amount of resin used: 208.2 mg (amount of resin introduced: 0.50 mmol/g);
Theoretical value of the peptide obtained by using this resin: 200.7 mg;
Crude amount actually obtained: 111.8 mg (yield: 55.7%).

Example 4

Preparation of Cationic Liposome, and pH-Responsiveness (1) Liposomes were prepared as follows. Specifically, a lipid ethanol solution prepared from a mixture of egg yolk phosphatidylcholine (EPC) and dioleoyl tetraammonium propane (DOTAP) at a molar ratio of 1:1 was dispensed into a test tube. An ethanol solution of peptide compound 1 obtained in Example 1 was added in an amount of 5 mol % of the total lipid content, and an equal amount of chloroform was mixed therewith, followed by evaporation to dryness under a stream of nitrogen to obtain a thin lipid membrane. A buffer having a pH of 7.4 was added thereto, and the mixture was sufficiently hydrated at room temperature for 10 minutes. After completion of hydration, the test tube was ultrasonicated using a water tank-type ultrasonic device to prepare liposome 1 comprising EPC, DOTAP, and peptide compound 1 (lipid concentration: 10 mM).

(2) The particle diameter (size) and surface potential (ζpotential) of liposome 1 diluted and suspended in buffer solutions having different pHs were measured by a Zetasizer Nano produced by Malvern Instruments Ltd. Further, the particle size and surface potential of a reference liposome (EPC/DOTAP=1/1 (molar ratio) into which no peptide compound had been introduced were also measured in the same manner. Table 2 shows the results.

TABLE 2

| | pH | | | |
|---|---|---|---|---|
| | 5.5 | 6.0 | 6.5 | 7.4 |
| (1) Liposome 1 | | | | |
| Size (nm) | 248 ± 30 | 243 ± 53 | 211 ± 44 | 110 ± 14 |
| ζ-potential (mV) | 21.2 ± 4.2 | 14.6 ± 2.9 | 9.8 ± 4.5 | −2.0 ± 2.2 |
| (2) Reference Liposome | | | | |
| Size (nm) | 117 | 117 | 116 | 119 |
| ζ-potential (mV) | 34.4 | 32.3 | 33.5 | 37.2 |

The results show that the pH-responsiveness of the reference liposome into which the peptide compound of the present invention had not been introduced was rarely changed in either of the particle diameter and the surface potential. In contrast, the particle diameter of the liposome into which the peptide compound of the present invention had been introduced was about 100 nm when the pH was 7.4. When the pH was 6.5, the particle diameter was increased about twice that when the pH was 7.4. Moreover, the surface potential was −2.0 mV when the pH was 7.4; however, the surface potential was changed to +9.8 mV when the pH was 6.5. These results suggest that the protonation of histidine contained in the peptide due to small pH changes leads to changes in the particle diameter and surface potential. The cause of the increase in the particle diameter when the pH was reduced from 7.4 to 6.5 is considered to be as follows. That is, the protonation of histidine induced a reduction of the hydrophobic interaction between hydrophobic regions and led to electrostatic repulsion between hydrophilic regions, whereby the liposome structure was loosened.

Test Example 1

Figure 7:
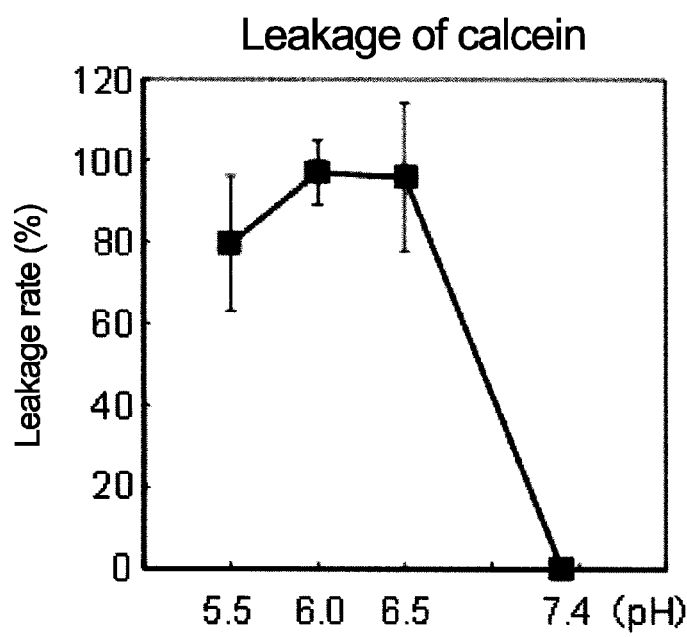
FIG. 7 shows the measurement results of the encapsulated drug leakage rate of calcein-encapsulated liposome 1 under different pH conditions.

Measurement of Leakage of Encapsulated Drugs under different pH conditions (1) After a peptide-containing lipid membrane was prepared as in Example 4, a calcein (Mw: 622.55) 30-mM solution was added, and calcein-encapsulated liposome 1 was prepared as in Example 4. Unencapsulated calcein was removed by gel filtration (Sephadex G50).
To measure the leakage of the encapsulated calcein from the liposomes, the liposomes were diluted and suspended in buffers having different pHs, and then incubated at 37° C. for 10 minutes. The fluorescence (λex: 488 nm, λem: 517 nm) of the leaked calcein was measured by a plate reader (Infinite M200, produced by Tecan). The fluorescence of the leaked calcein when the liposomes were mixed with 1% Triton-X100 was regarded as complete leakage. The leakage rate was calculated by the following formula. FIG. 7 shows the results.

Leakage rate(%)=$(F_{sample}-F_{pH\ 7.4})/(F_{triton}-F_{pH\ 7.4}) \times 100$ $F_{sample}$: Fluorescence of calcein leaked from the liposomes at each pH $F_{pH\ 7.4}$: Fluorescence of calcein leaked from the liposomes at a pH of 7.4

$F_{triton}$: Fluorescence of calcein when the liposomes were mixed with 1% Triton-X100.

The results show that no leakage was observed at a pH of 7.4, whereas leakage of about 100% calcein was observed at a pH of 6.5. This suggested that the His of the hydrophilic block and hydrophobic block of the peptide compound embedded in the lipid membrane was protonated due to small pH changes, which caused repulsion between the peptide and the lipid molecules, thereby allowing leakage of the encapsulated calcein.

Figure 8:
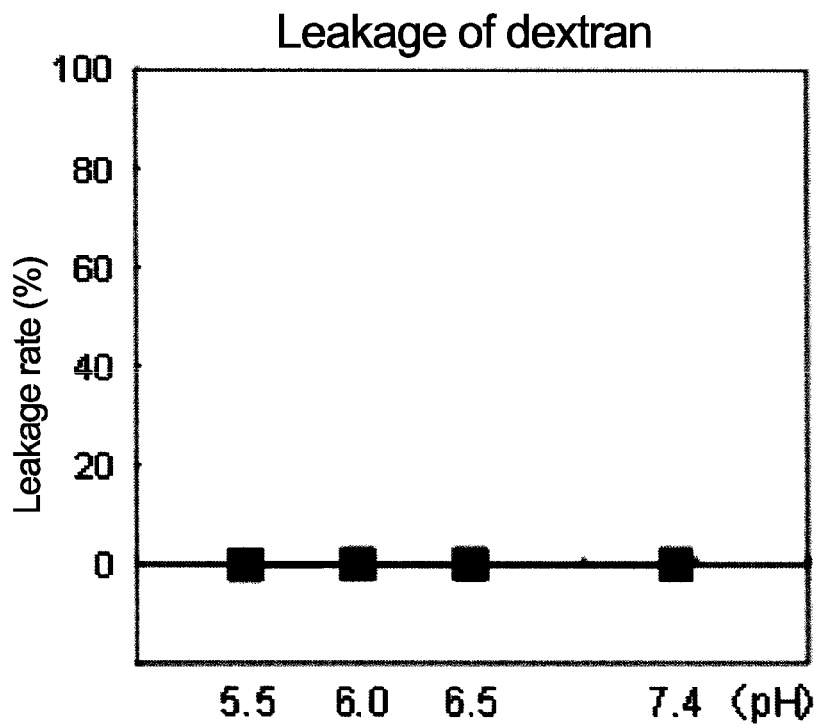
FIG. 8 shows the measurement results of the encapsulated drug leakage rate of Texas Red-labeled dextran-encapsulated liposome 1 under different pH conditions.

(2) After a peptide-containing lipid membrane was prepared as in Example 4, a Texas Red-labeled dextran (Mw 3,000) 2-mg/ml solution was added, and dextran-encapsulated liposome 1 was prepared as in Example 4. In order to increase the encapsulation rate of the Texas Red-labeled dextran into the liposome, freezing with liquid nitrogen was performed, followed by thawing at 37° C. The freezing-thawing process was repeated 5 times. Unencapsulated Texas Red-labeled dextran was removed by gel filtration (Sepharose CL-6B). Leakage of the encapsulated Texas Red-labeled dextran from the liposome was measured in the same manner as described above. FIG. 8 shows the results.

The results show that no leakage was observed at a pH of 7.4, and no leakage of dextran from the liposome was observed even at a pH of 6.5 or less. This suggested that this liposome could selectively leak a low-molecular-weight compound, without leaking a high-molecular-weight compound, depending on small pH changes.

Figure 9:
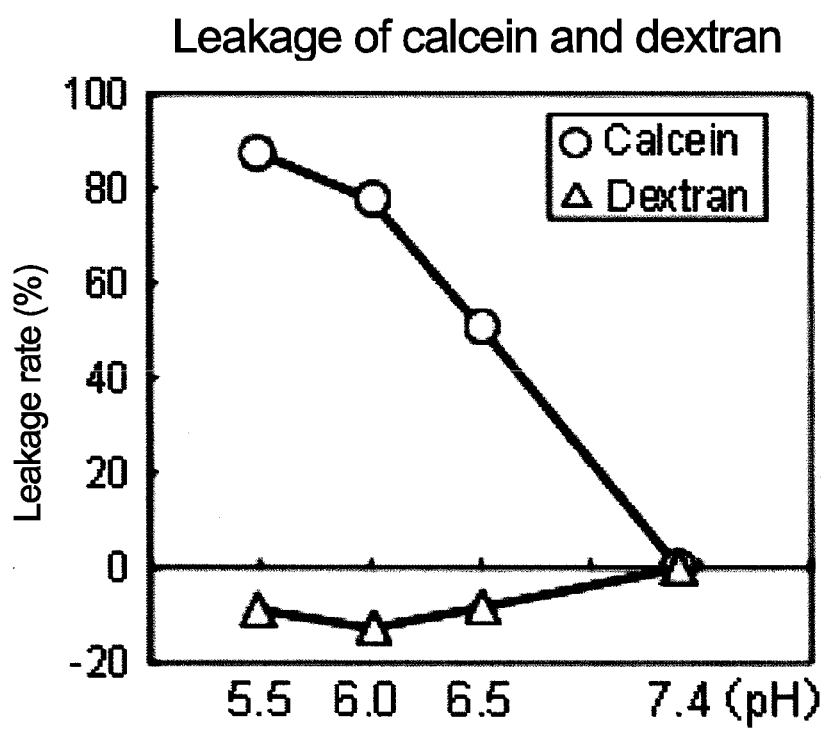
FIG. 9 shows the measurement results of the encapsulated drug leakage rates of calcein- and Texas Red-labeled dextran-encapsulated liposome 1 under different pH conditions.

(3) After a peptide-containing lipid membrane was prepared as in Example 4, a calcein (Mw 622.55) 15-mM solution and a Texas Red-labeled dextran (Mw 3,000) 1-mg/ml solution were added, and two-component-encapsulated liposome 1 was prepared as in Example 4. Unencapsulated calcein and dextran were removed by dialysis using a dialysis membrane (molecular cut-off: 14,000). Leakage of the encapsulated Texas Red-labeled dextran and calcein from the liposome was measured in the same manner as described above. FIG. 9 shows the results.

The results show that when calcein and dextran were encapsulated together in the liposome, leakage of calcein was about 60% at a pH of 6.5, and about 80% at a pH of 6.0 or less. On the other hand, no leakage of dextran was observed at all pHs. This confirmed that this liposome could selectively leak a low-molecular-weight compound depending on small pH changes, as described above.

The liposome of the present invention can leak a low-molecular-weight compound in a pH-dependent manner. When compounds having different molecular weights are encapsulated in the liposome of the present invention, the compounds can be gradually leaked according to their molecular weights.

Test Example 2

CD spectra of peptide alone or peptide-introduced liposome under different pH conditions (presenting pH-responsiveness and the necessity of a membrane structure substrate)

Figure 10:
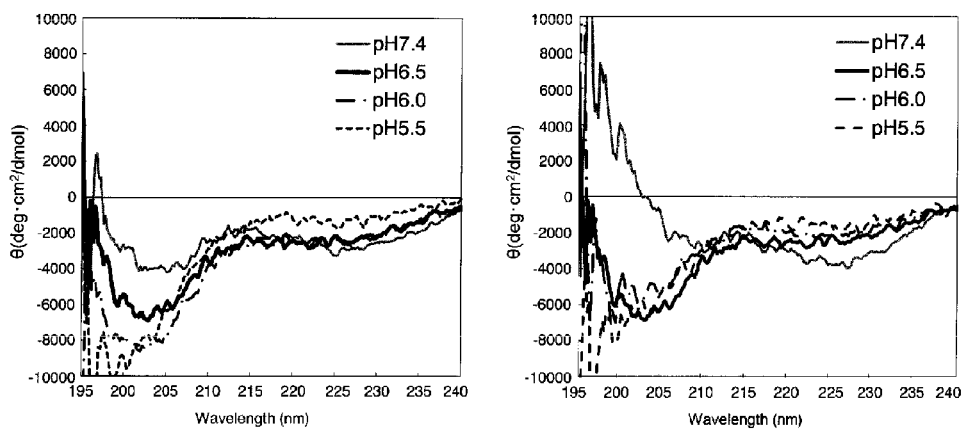
FIG. 10 shows the CD spectra of peptide compound 1 alone, and the CD spectra of a peptide-introduced liposome.

Peptide compound 1 obtained in Example 1 alone and a peptide-introduced liposome obtained according to Example 4 (each having a peptide concentration of 20 μM) were suspended in PBS (−) with different pHs, and CD (circular dichroism) spectra were recorded on a J-720WI spectropolarimeter (produced by JASCO Corporation). FIG. 10 shows the results.

The "α-helix" represents an α-helix structure, and the "random coil structure" represents a state in which a clear secondary structure is not formed.

The results show that the structure of peptide compound 1 alone was α-helix (a positive peak at around 196 nm, and negative peaks at around 207 and 222 nm) at a pH of 7.4; however, it was sequentially converted into a random coil structure (a negative peak at around 196 nm), as the pH was reduced. In contrast, the structure of the peptide-introduced liposome was similarly α-helix at a pH of 7.4; however, it was nearly completely converted into a random coil structure at a pH of 6.5. Thus, the peptide alone and the peptide-introduced liposome underwent different structural transitions associated with pH changes. These results suggest that a membrane structure substrate is essential for the pH responsiveness of peptides.

Example 5

Preparation of Liposomes Having Different Lipid Compositions (1) Neutral liposome 2 (EPC/peptide compound 1=1/5 mol %) was prepared as in Example 4.
(2) Anionic liposome 3 (EPC/DSPG/peptide compound 1=1/1/5 mol %) was prepared as in Example 4.

Test Example 3

Measurement of the Leakage of Drugs Encapsulated in Various Liposomes

Calcein was encapsulated in liposome 1 obtained in Example 4, and liposomes 2 and 3 obtained in Example 5, and pH responsiveness was examined as in Test Example 1. The results show that no leakage of calcein from any of the liposomes was observed at a pH of 7.4; however, at a pH of 6.5, cationic liposome 1 showed the highest leakage. The leakage was reduced in the order of anionic liposome 3 and neutral liposome 2. This suggested that it was most preferable to introduce a peptide compound into cationic liposomes so that the liposomes exhibited responsiveness at a slightly acidic pH.

Example 6

Liposome 2 into which peptide compound 2 obtained in Example 2 had been introduced was produced according to the method described in Example 4, and calcein-encapsulated liposome 2 was prepared by the same production method as in Test Example 1.

Example 7

Liposome 3 into which peptide compound 3 obtained in Example 3 had been introduced was produced according to the method described in Example 4, and calcein-encapsulated liposome 3 was prepared by the same production method as in Test Example 1.

Comparative Example 4

Comparative liposome 1 into which comparative compound 1 obtained in Comparative Example 1 had been introduced was produced according to the method described in Example 4, and calcein-encapsulated comparative liposome 1 was prepared by the same production method as in Test Example 1.

Comparative Example 5

Comparative liposome 2 into which comparative compound 2 obtained in Comparative Example 2 had been introduced was produced according to the method described in Example 4, and calcein-encapsulated comparative liposome 2 was prepared by the same production method as in Test Example 1.

Comparative Example 6

Comparative liposome 3 into which comparative compound 3 obtained in Comparative Example 3 had been introduced was produced according to the method described in Example 4, and calcein-encapsulated comparative liposome 3 was prepared by the same production method as in Test Example 1.

Test Example 4

Average Hydropathy Index of Peptide-Introduced Liposome, and Encapsulated Drug Leakage Rate The calcein leakage rate of the calcein-encapsulated liposomes obtained in Examples 4, 6, and 7, and Comparative Examples 4 to 6 at a pH of 7.4 and a pH of 6.5 was calculated as in Test Example 1. Table 3 shows the results.

phobic block of the peptide had been introduced, and the liposome into which comparative compound 2, whose average hydropathy index was changed by changing the ratio of the number of amino acids in the hydrophilic block and hydrophobic block of the peptide compound to 1:1, had been introduced, the leakage of the encapsulated drugs was remarkably reduced, even when the pH was changed from 7.4 to 6.5. Thus, the pH-responsiveness was insufficient. Further, liposomes into which comparative compound 3 having four fewer residues than peptide compound 1 had been introduced were prepared; however, they were remarkably aggregated at a pH of 6.5 or less. Moreover, an attempt was made to encapsulate calcein into the liposomes; however, fluorescence intensity at the same level as that when Triton treatment was performed was observed at a pH of 7.4. This suggested that the liposomes containing the peptide having a sequence with four fewer residues were unstable, and that a drug could not be encapsulated therein.

Test Example 5

Antitumor Effect of Doxorubicin (Dox)-Encapsulated Liposome 4

Dox-encapsulated liposome 4 was prepared as follows. Specifically, a lipid ethanol solution prepared from a mixture of egg yolk phosphatidylcholine (EPC) and dioleoyl tetraammonium propane (DOTAP) at a molar ratio of 1:1 was dispensed into a test tube. An ethanol solution of peptide compound 1 obtained in Example 1 was added in an amount of 5 mol % of the total lipid content, and an ethanol solution

TABLE 3

| Compound | Amino acid sequence (hydrophilic block)-(hydrophobic block) | Average hydropathy index Hydrophilic block | Average hydropathy index Hydrophobic block | Number of residues | Calcein leakage rate (%) pH 7.4 | Calcein leakage rate (%) pH 6.5 |
|---|---|---|---|---|---|---|
| Peptide compound 1 | HGHG-LALLAHALLAHAALAHAALA | −1.8 | 1.75 | 24 | 0 | 100 |
| Peptide compound 2 | GHHG-LALLHALHLAAAALHAAALA | −1.8 | 1.75 | 24 | 0 | 90 |
| Peptide compound 3 | EGEG-LALLAHALLAHAALAHAALA | −1.95 | 1.75 | 24 | 0 | 65 |
| Comparative compound 1 | HHGG-LLLLHHHAAAAALLLAAAAA | −1.8 | 1.75 | 24 | 0 | 30 |
| Comparative compound 2 | HGHGGGGGGGGG-AHALLAHAALAH | −0.87 | 1.05 | 24 | 0 | 30 |
| Comparative compound 3 | HGHG-LALLAHALLAHAAAL | −1.8 | 1.925 | 20 | — | — |

The results show that in the liposomes into which the peptide compounds of the present invention had been introduced, no leakage was observed under physiological conditions of pH 7.4; however, high leakage (60% or more) of the encapsulated drug was observed at a weakly acidic pH of 6.5. In particular, significantly high leakage of the encapsulated drug was observed in the peptide compounds having His in the hydrophilic amino acid block and hydrophobic amino acid block. In contrast, even with the same constituent amino acids, in the liposome into which comparative compound 1 having adjacent histidine residues in the hydroof polyethylene glycol-distearoyl phosphatidylethanolamine (PEG-DSPE) was further added in an amount of 5 mol % of the total lipid content. An equal amount of chloroform was further mixed therewith, followed by evaporation to dryness under a stream of nitrogen to obtain a thin lipid membrane. Subsequently, 250 mM ammonium sulfate (pH 8.5) was added thereto, and the mixture was sufficiently hydrated at room temperature for 10 minutes. After completion of hydration, the test tube was ultrasonicated using a water tank-type ultrasonic device to prepare liposome 4 comprising EPC, DOTAP, PEG-DSPE, and peptide compound 1

(lipid concentration: 10 mM). The prepared liposome 4 was subjected to gel filtration using a Sephadex G-50 column equilibrated with 10% sucrose (pH 8.5). The lipid concentration in the collected fractions was quantified using Phospholipid Test Wako. A Dox solution (2 mg/ml) was added to liposome 4, and the mixture was incubated at 65° C. for 1 hour. Then, unencapsulated Dox was removed by gel filtration using a Sephadex G-50 column. The amount of Dox encapsulated in liposome 4 was quantified by solubilizing the liposome with Triton-X treatment, and then measuring the absorbance at 490 nm using a plate reader (Infinite M200, produced by Tecan).

To evaluate the antitumor effect of Dox-encapsulated liposome 4, a Dox solution or Dox-encapsulated liposome 4 was administered to tumor-bearing hairless mice in which the tumor formed from subcutaneously implanted B16-F1 cells grew to a size of 100 mm$^3$, by tail vein injection at a Dox concentration of 0.5 mg/kg per injection 5, 8, 12, or 15 days after implantation. The tumor volume was calculated from the length and width of the tumor using the following formula:

(Tumor volume)=0.5×(length)×(width)$^2$

Further, the relative tumor volume was calculated by the following formula:

(Relative tumor volume)=(tumor volume 8,12,15, or 19 days after implantation)/(tumor volume 5 days after implantation)

Figure 11:
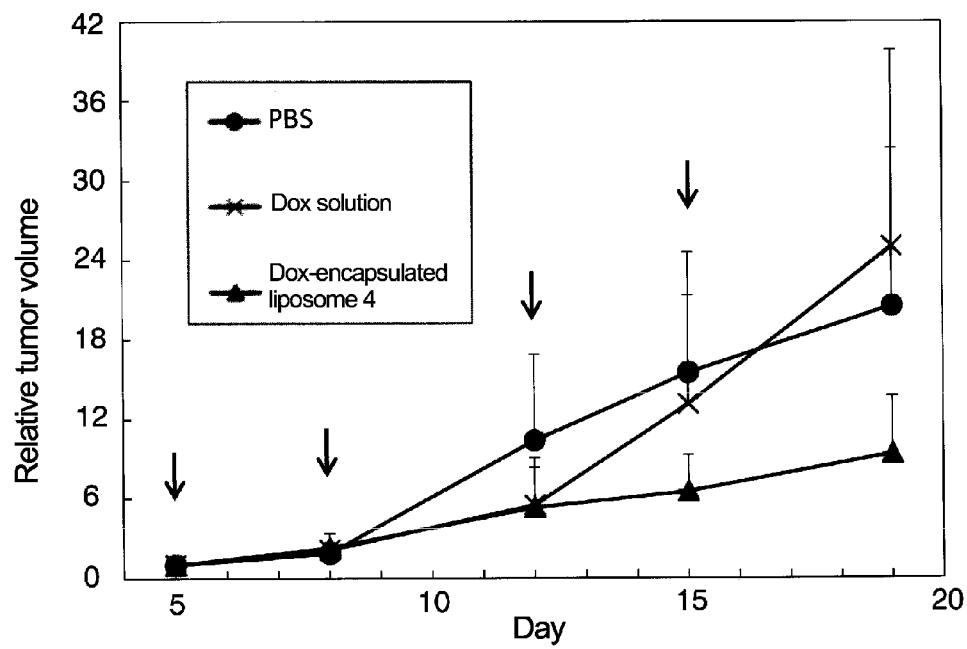
FIG. 11 shows the antitumor effects of doxorubicin (Dox) alone and the antitumor effects of a Dox-encapsulated liposome in Test Example 5.

FIG. 11 shows the results. As shown in FIG. 11, when low-dose Dox was administered, Dox-encapsulated liposome 4 showed a higher tumor growth inhibitory effect than that of the Dox solution.

The invention claimed is:

1. A peptide compound comprising a hydrophilic amino acid block and a hydrophobic amino acid block;
   [1] the peptide compound consisting of 24 to 36 amino acids in total;
   [2] the hydrophilic amino acid block consisting of 4 to 10 amino acids in total and having an average hydropathy index of −3.0 to −1.0; and
   [3] the hydrophobic amino acid block consisting of 20 to 32 amino acids in total, containing one or more His residues, and having an average hydropathy index of 1.0 to 2.5;
   wherein when the hydrophobic amino acid block comprises two or more amino acids having a hydropathy index of −3.0 or less, amino acids having a hydropathy index of −3.0 or less are not adjacent to each other in the hydrophobic amino acid block.

2. The peptide compound according to claim 1, wherein the hydrophilic amino acid block has an average hydropathy index of −2.0 to −1.5; and
   the hydrophobic amino acid block has an average hydropathy index of 1.5 to 2.0.

3. The peptide compound according to claim 1, wherein the hydrophilic amino acid block comprises an amino acid having a hydropathy index of −3.0 or less and an amino acid having a hydropathy index of 0 to −1.0; and
   the hydrophobic amino acid block comprises His and an amino acid having a hydropathy index of higher than 0.

4. The peptide compound according to claim 1, wherein the amino acids constituting the hydrophilic amino acid block are His or Glu, and Gly; and the amino acids constituting the hydrophobic amino acid block are His and any amino acid selected from the group consisting of Leu, Ala, Met, Cys, Phe, Val, and Ile.

5. The peptide compound according to claim 1, wherein the hydrophilic amino acid block has a peptide sequence containing 0 to 5 His residues; and
   the hydrophobic amino acid block has a peptide sequence containing 1 to 8 His residues.

6. The peptide compound according to claim 1, wherein the hydrophilic amino acid block is represented by the following formula (I):

$$(AA_1)(AA_2)(AA_3)(AA_4) \quad (I)$$

wherein any two of $AA_1$, $AA_2$, $AA_3$, and $AA_4$ are His or Glu, and the other two are Gly; and
the hydrophobic amino acid block contains 5 to 8 units represented by the following formula (II):

$$(AA_5)(AA_6)(AA_7)(AA_8) \quad (II)$$

wherein $AA_5$, $AA_6$, $AA_7$, and $AA_8$ are the same or different, and each represents His, Leu, or Ala, with the proviso that at least one of the units of the formula (II) contains one or two His residues; each unit may have the same or different amino acid sequence.

7. A liposome comprising the peptide compound according to claim 1, and a lipid.

8. The liposome according to claim 7, wherein the liposome comprises 1 to 10 mol % of the peptide compound based on the total amount of lipids in the liposome.

9. The liposome according to claim 8, wherein the liposome is a cationic liposome.

10. The liposome according to claim 7, wherein the liposome encapsulates a target substance.

11. A pharmaceutical composition comprising the liposome according to claim 10, in combination with a pharmaceutically acceptable carrier, wherein said target substance is selected from the group consisting of drugs, nucleic acids, peptides, and proteins.

12. An antitumor agent comprising the liposome according to claim 10, wherein said target substance is an anticancer agent.

13. The antitumor agent according to claim 12, wherein said cancer agent is selected from the group consisting of tegafur, doxorubicin, daunorubicin, cis-platinum, oxaliplatin, carboplatin, paclitaxel, irinotecan, SN-38, actinomycin D, vincristine, vinblastine, methotrexate, fluorouracil, mitomycin C, docetaxel, cyclophosphamide, capecitabine, epirubicin, gemcitabine, mitoxantrone, leucovorin, vinorelbine, trastuzumab, etoposide, estramustine, prednisone, interferon .alpha., interleukin-2, bleomycin, ifosfamide, mesna, altretamine, topotecan, cytarabine, methylprednisolone, dexamethasone, mercaptopurine, thioguanine, fludarabine, gemtuzumab, idarubicin, mitoxantrone, tretinoin, alemtuzumab, chlorambucil, cladribine, imatinib, epirubicin, dacarbazine, procarbazine, mechlorethamine, rituximab, denileukin diftitox, allopurinol, carmustine, tamoxifen, filgrastim, temozolomide, melphalan, vinorelbine, azacitidine, thalidomide, and mitomycin.

14. The pharmaceutical composition according to claim 11, wherein said liposome further comprises sugars.

15. A peptide compound comprising a hydrophilic amino acid block and a hydrophobic amino acid block; wherein
 a) the peptide compound consists of 24 to 36 amino acids in total;
 b) the hydrophilic amino acid block consists of 4 to 10 amino acids in total and has an average hydropathy index of −3.0 to −1.0; and
 c) the hydrophobic amino acid block consists of 20 to 32 amino acids in total, containing one or more His residues, and having an average hydropathy index of 1.0 to 2.5,
 wherein the hydrophobic amino acid block contains 5 to 8 units represented by the following formula (II):

$$(AA_5)(AA_6)(AA_7)(AA_8) \tag{II}$$

wherein $AA_5$, $AA_6$, $AA_7$, and $AA_8$ are the same or different, and each represents His, Leu, or Ala, wherein when the hydrophobic amino acid block contains two or more His residues, no His residues between the units or in each unit are adjacent to each other; and wherein each unit may have the same or different amino acid sequences.

16. A liposome comprising the peptide compound according to claim 15, and a lipid.

* * * * *

SEQUENCE LISTING

```
<160> NUMBER OF SEQ ID NOS: 6

<210> SEQ ID NO 1
<211> LENGTH: 24
<212> TYPE: PRT
<213> ORGANISM: Artificial
<220> FEATURE:
<223> OTHER INFORMATION: Synthetic peptide

<400> SEQUENCE: 1

His Gly His Gly Leu Ala Leu Leu Ala His Ala Leu Leu Ala His Ala
1               5                   10                  15

Ala Leu Ala His Ala Ala Leu Ala
            20

<210> SEQ ID NO 2
<211> LENGTH: 24
<212> TYPE: PRT
<213> ORGANISM: Artificial
<220> FEATURE:
<223> OTHER INFORMATION: Synthetic peptide

<400> SEQUENCE: 2

Gly His His Gly Leu Ala Leu Leu His Ala Leu His Leu Ala Ala Ala
1               5                   10                  15

Ala Leu His Ala Ala Ala Leu Ala
            20

<210> SEQ ID NO 3
<211> LENGTH: 24
<212> TYPE: PRT
<213> ORGANISM: Artificial
<220> FEATURE:
<223> OTHER INFORMATION: Synthetic peptide

<400> SEQUENCE: 3

Glu Gly Glu Gly Leu Ala Leu Leu Ala His Ala Leu Leu Ala His Ala
1               5                   10                  15

Ala Leu Ala His Ala Ala Leu Ala
            20

<210> SEQ ID NO 4
<211> LENGTH: 24
<212> TYPE: PRT
<213> ORGANISM: Artificial
<220> FEATURE:
<223> OTHER INFORMATION: Synthetic peptide
```

```
<400> SEQUENCE: 4

His His Gly Gly Leu Leu Leu Leu His His His Ala Ala Ala Ala Ala
1               5                   10                  15

Leu Leu Leu Ala Ala Ala Ala Ala
            20

<210> SEQ ID NO 5
<211> LENGTH: 24
<212> TYPE: PRT
<213> ORGANISM: Artificial
<220> FEATURE:
<223> OTHER INFORMATION: Synthetic peptide

<400> SEQUENCE: 5

His Gly His Gly Gly Gly Gly Gly Gly Gly Gly Ala His Ala Leu
1               5                   10                  15

Leu Ala His Ala Ala Leu Ala His
            20

<210> SEQ ID NO 6
<211> LENGTH: 20
<212> TYPE: PRT
<213> ORGANISM: Artificial
<220> FEATURE:
<223> OTHER INFORMATION: Synthetic peptide

<400> SEQUENCE: 6

His Gly His Gly Leu Ala Leu Leu Ala His Ala Leu Leu Ala His Ala
1               5                   10                  15

Ala Ala Ala Leu
            20
```